United States Patent
Boileau et al.

(10) Patent No.: US 10,413,416 B2
(45) Date of Patent: Sep. 17, 2019

(54) METHOD AND APPARATUS FOR FITTING A SHOULDER PROSTHESIS

(71) Applicant: Tornier SAS, Montbonnot Saint Martin (FR)

(72) Inventors: Pascal Boileau, Nice (FR); Gilles Walch, Lyons (FR)

(73) Assignee: Tornier SAS, Montbonnot Saint Martin (FR)

( * ) Notice: Subject to any disclaimer, the term of this patent is extended or adjusted under 35 U.S.C. 154(b) by 0 days.

(21) Appl. No.: 15/338,188

(22) Filed: Oct. 28, 2016

(65) Prior Publication Data

US 2017/0042687 A1    Feb. 16, 2017

Related U.S. Application Data

(60) Continuation of application No. 14/495,703, filed on Sep. 24, 2014, now Pat. No. 10,251,755, which is a
(Continued)

(51) Int. Cl.
*A61F 2/40* (2006.01)
*A61F 2/28* (2006.01)
(Continued)

(52) U.S. Cl.
CPC ........ *A61F 2/4003* (2013.01); *A61B 17/1635* (2013.01); *A61B 17/1637* (2013.01);
(Continued)

(58) Field of Classification Search
CPC ........ A61F 2/4081; A61F 2/4014; A61F 2/40; A61F 2/4059; A61F 2/4612; A61F 2002/30332
See application file for complete search history.

(56) References Cited

U.S. PATENT DOCUMENTS

| | | | |
|---|---|---|---|
| 2,666,430 A | 1/1954 | Gispert | |
| 3,412,733 A | 11/1968 | Ross | |

(Continued)

FOREIGN PATENT DOCUMENTS

| | | |
|---|---|---|
| CH | 426096 | 12/1966 |
| CH | 507704 | 5/1971 |

(Continued)

OTHER PUBLICATIONS

"Aequalis-Fracture Shoulder Prosthesis—Surgical Technique," Tornier, Inc., in 32 pages.
(Continued)

*Primary Examiner* — Ann Schillinger
(74) *Attorney, Agent, or Firm* — Knobbe, Martens, Olson & Bear LLP

(57) ABSTRACT

Method and set of surgical instruments for fitting a shoulder prosthesis, and the shoulder prosthesis. The proposed method seeks to interpose a bone graft between the previously prepared glenoid surface (G) of a scapula (S) of a patient's shoulder and the face of a glenoid prosthetic component opposite the articular surface. The set of instruments permit the bone graft to be taken from the upper epiphysis of the humerus (H), either in situ or ex vivo.

8 Claims, 15 Drawing Sheets

Related U.S. Application Data division of application No. 12/020,913, filed on Jan. 28, 2008, now Pat. No. 8,864,834.

(60) Provisional application No. 60/888,437, filed on Feb. 6, 2007, provisional application No. 60/971,762, filed on Sep. 12, 2007, provisional application No. 61/015,042, filed on Dec. 19, 2007.

(51) Int. Cl.
| | |
|---|---|
| *A61B 17/16* | (2006.01) |
| *A61F 2/30* | (2006.01) |
| *A61F 2/46* | (2006.01) |
| *A61B 17/17* | (2006.01) |
| *A61B 17/86* | (2006.01) |

(52) U.S. Cl.
CPC ...... *A61B 17/1684* (2013.01); *A61B 17/1778* (2016.11); *A61F 2/28* (2013.01); *A61F 2/30734* (2013.01); *A61F 2/40* (2013.01); *A61F 2/4081* (2013.01); *A61F 2/4612* (2013.01); *A61F 2/4644* (2013.01); *A61B 17/1615* (2013.01); *A61B 17/86* (2013.01); *A61F 2/30767* (2013.01); *A61F 2002/2817* (2013.01); *A61F 2002/2835* (2013.01); *A61F 2002/302* (2013.01); *A61F 2002/30225* (2013.01); *A61F 2002/30433* (2013.01); *A61F 2002/30448* (2013.01); *A61F 2002/30677* (2013.01); *A61F 2002/30736* (2013.01); *A61F 2002/30878* (2013.01); *A61F 2002/30884* (2013.01); *A61F 2002/30911* (2013.01); *A61F 2002/4022* (2013.01); *A61F 2002/4085* (2013.01); *A61F 2220/005* (2013.01); *A61F 2220/0041* (2013.01); *A61F 2230/0065* (2013.01); *A61F 2230/0069* (2013.01); *A61F 2310/00359* (2013.01); *A61F 2310/00796* (2013.01)

(56) References Cited

U.S. PATENT DOCUMENTS

| | | |
|---|---|---|
| 3,694,820 A | 10/1972 | Scales et al. |
| 3,815,157 A | 6/1974 | Skorecki et al. |
| 3,842,442 A | 10/1974 | Kolbel |
| 3,864,758 A | 2/1975 | Yakich |
| 3,869,730 A | 3/1975 | Skobel |
| 3,916,451 A | 11/1975 | Buechel et al. |
| 3,978,528 A | 9/1976 | Buechel et al. |
| 3,979,778 A | 9/1976 | Stroot |
| 3,992,726 A | 11/1976 | Freeman et al. |
| 4,003,095 A | 1/1977 | Gristina |
| 4,030,143 A | 6/1977 | Elloy et al. |
| 4,040,131 A | 8/1977 | Gristina |
| 4,054,955 A | 10/1977 | Seppo |
| 4,126,924 A | 11/1978 | Akins et al. |
| 4,131,116 A | 12/1978 | Hendrick |
| 4,135,517 A | 1/1979 | Reale |
| 4,179,758 A | 12/1979 | Gristina |
| 4,206,517 A | 6/1980 | Pappas et al. |
| 4,261,062 A | 4/1981 | Amstutz et al. |
| 4,479,271 A | 10/1984 | Bolesky et al. |
| 4,550,450 A | 11/1985 | Kinnett |
| 4,662,891 A | 5/1987 | Noiles |
| 4,693,723 A | 9/1987 | Gabard |
| 4,822,370 A | 4/1989 | Schelhas |
| 4,846,840 A | 7/1989 | Leclercq et al. |
| 4,865,605 A | 9/1989 | Dines et al. |
| 4,865,609 A | 9/1989 | Roche |
| 4,892,549 A | 1/1990 | Figgie, III et al. |
| 4,919,670 A | 4/1990 | Dale et al. |
| 4,957,510 A | 9/1990 | Cremascoli |
| 4,963,155 A | 10/1990 | Lazzeri et al. |
| 4,964,865 A | 10/1990 | Burkhead et al. |
| 5,030,233 A | 7/1991 | Ducheyne |
| 5,032,132 A | 7/1991 | Matsen, III et al. |
| 5,053,050 A | 10/1991 | Italy |
| 5,080,673 A | 1/1992 | Burkhead et al. |
| 5,080,685 A | 1/1992 | Bolesky et al. |
| 5,127,920 A | 7/1992 | MacArthur |
| 5,135,529 A | 8/1992 | Paxson et al. |
| 5,163,961 A | 11/1992 | Harwin |
| 5,181,928 A | 1/1993 | Bolesky et al. |
| 5,192,329 A | 3/1993 | Christie et al. |
| 5,201,882 A | 4/1993 | Paxson |
| 5,206,925 A | 4/1993 | Nakazawa et al. |
| 5,222,984 A | 6/1993 | Forte |
| 5,261,914 A | 11/1993 | Warren |
| 5,314,479 A | 5/1994 | Rockwood et al. |
| 5,314,487 A | 5/1994 | Schryver et al. |
| 5,330,531 A | 7/1994 | Capanna |
| 5,358,526 A | 10/1994 | Tornier |
| 5,383,936 A | 1/1995 | Kubein Meesenburg et al. |
| 5,425,779 A | 6/1995 | Schlosser et al. |
| 5,443,515 A | 8/1995 | Cohen et al. |
| 5,443,519 A | 8/1995 | Averill et al. |
| 5,462,563 A | 10/1995 | Shearer et al. |
| 5,507,817 A | 4/1996 | Craig et al. |
| 5,507,818 A | 4/1996 | McLaughlin |
| 5,507,824 A | 4/1996 | Lennox |
| 5,534,033 A | 7/1996 | Simpson |
| 5,549,682 A | 8/1996 | Roy |
| 5,580,352 A | 12/1996 | Sekel |
| 5,702,447 A | 12/1997 | Walch et al. |
| 5,702,457 A | 12/1997 | Walch et al. |
| 5,702,486 A | 12/1997 | Craig et al. |
| 5,723,018 A | 3/1998 | Cyprien et al. |
| 5,728,161 A | 3/1998 | Camino et al. |
| 5,741,335 A | 4/1998 | Gerber et al. |
| 5,755,719 A | 5/1998 | Frieze et al. |
| 5,755,807 A | 5/1998 | Anstaett et al. |
| 5,779,709 A | 7/1998 | Harris et al. |
| 5,800,551 A | 9/1998 | Williamson et al. |
| 5,800,557 A | 9/1998 | Elhami |
| 5,879,355 A | 3/1999 | Ullmark |
| 5,879,405 A | 3/1999 | Ries et al. |
| 5,902,340 A | 5/1999 | White et al. |
| 5,910,171 A | 6/1999 | Kummer et al. |
| 5,928,285 A | 7/1999 | Bigliani et al. |
| 5,944,758 A | 8/1999 | Mansat et al. |
| 5,961,555 A | 10/1999 | Huebner |
| 5,972,368 A * | 10/1999 | McKay .............. A61L 27/3608 424/422 |
| 5,984,927 A | 11/1999 | Wenstrom et al. |
| 6,015,437 A | 1/2000 | Stossel |
| 6,027,503 A | 2/2000 | Khalili et al. |
| 6,033,439 A | 3/2000 | Camino et al. |
| 6,045,302 A | 4/2000 | Orr |
| 6,045,582 A | 4/2000 | Prybyla |
| 6,045,583 A | 4/2000 | Gross et al. |
| 6,090,145 A | 7/2000 | Hassler et al. |
| 6,102,953 A | 8/2000 | Huebner |
| 6,129,764 A | 10/2000 | Servidio |
| 6,165,224 A | 12/2000 | Tornier |
| 6,171,341 B1 | 1/2001 | Boileau et al. |
| 6,197,062 B1 | 3/2001 | Fenlin |
| 6,197,063 B1 | 3/2001 | Dews |
| 6,203,575 B1 | 3/2001 | Farey |
| 6,206,925 B1 | 3/2001 | Tornier |
| 6,221,076 B1 | 4/2001 | Albrektsson et al. |
| 6,228,120 B1 | 5/2001 | Leonard et al. |
| 6,245,074 B1 | 6/2001 | Allard et al. |
| 6,267,767 B1 | 7/2001 | Strobel et al. |
| 6,283,999 B1 | 9/2001 | Rockwood |
| 6,312,467 B1 | 11/2001 | McGee |
| 6,334,874 B1 | 1/2002 | Tornier |
| 6,364,910 B1 | 4/2002 | Shultz et al. |
| 6,368,352 B1 | 4/2002 | Camino et al. |
| 6,368,353 B1 | 4/2002 | Arcand |
| 6,398,812 B1 | 6/2002 | Masini |
| 6,406,495 B1 | 6/2002 | Schoch |

(56) References Cited

U.S. PATENT DOCUMENTS

| | | |
|---|---|---|
| 6,406,496 B1 | 6/2002 | Rüter |
| 6,436,144 B1 | 8/2002 | Ahrens |
| 6,436,146 B1 | 8/2002 | Hassler et al. |
| 6,436,147 B1 | 8/2002 | Zweymüller |
| 6,454,811 B1 | 9/2002 | Sherwood et al. |
| 6,458,136 B1 | 10/2002 | Allard et al. |
| 6,475,221 B1 | 11/2002 | White et al. |
| 6,475,243 B1 | 11/2002 | Sheldon et al. |
| 6,494,913 B1 | 12/2002 | Huebner |
| 6,506,214 B1 | 1/2003 | Gross |
| 6,508,840 B1 | 1/2003 | Rockwood et al. |
| 6,511,511 B1 | 1/2003 | Slivka et al. |
| 6,514,287 B2 | 2/2003 | Ondrla et al. |
| 6,520,994 B2 | 2/2003 | Nogarin |
| 6,530,957 B1 | 3/2003 | Jack |
| 6,541,022 B1 | 4/2003 | Murphy et al. |
| 6,558,425 B2 | 5/2003 | Rockwood |
| 6,569,202 B2 | 5/2003 | Whiteside |
| 6,589,281 B2 | 7/2003 | Hyde, Jr. |
| 6,605,117 B2 | 8/2003 | Kuberasampath et al. |
| 6,620,197 B2 | 9/2003 | Maroney et al. |
| 6,626,946 B1 | 9/2003 | Walch et al. |
| 6,673,114 B2 | 1/2004 | Hartdegen et al. |
| 6,673,115 B2 | 1/2004 | Resch et al. |
| 6,679,916 B1 | 1/2004 | Frankle et al. |
| 6,692,563 B2 | 2/2004 | Zimmermann |
| 6,730,252 B1 | 5/2004 | Teoh et al. |
| 6,736,851 B2 | 5/2004 | Maroney et al. |
| 6,746,487 B2 | 6/2004 | Scifert et al. |
| 6,749,637 B1 | 6/2004 | Bähler |
| 6,755,866 B2 | 6/2004 | Southworth |
| 6,761,740 B2 | 7/2004 | Tornier |
| 6,767,928 B1 | 7/2004 | Murphy et al. |
| 6,780,190 B2 | 8/2004 | Maroney |
| 6,783,549 B1 | 8/2004 | Stone et al. |
| 6,790,234 B1 | 9/2004 | Frankle |
| 6,797,006 B2 | 9/2004 | Hodorek |
| 6,863,690 B2 | 3/2005 | Ball et al. |
| 6,875,234 B2 | 4/2005 | Lipman et al. |
| 6,887,277 B2 | 5/2005 | Rauscher et al. |
| 6,890,358 B2 | 5/2005 | Ball et al. |
| 6,902,584 B2 | 6/2005 | Kwan et al. |
| 6,942,699 B2 | 9/2005 | Stone et al. |
| 6,953,478 B2 | 10/2005 | Bouttens et al. |
| 6,969,406 B2 | 11/2005 | Tornier |
| 7,011,686 B2 | 3/2006 | Ball et al. |
| 7,033,395 B2 | 4/2006 | Tornier |
| 7,051,417 B2 | 5/2006 | Michelson |
| 7,066,959 B2 | 6/2006 | Errico et al. |
| 7,108,719 B2 | 9/2006 | Horber |
| 7,166,132 B2 | 1/2007 | Callaway et al. |
| 7,169,184 B2 | 1/2007 | Dalla Pria |
| 7,175,663 B1 | 2/2007 | Stone |
| 7,195,645 B2 | 3/2007 | Disilvestro et al. |
| 7,238,207 B2 | 7/2007 | Blatter et al. |
| 7,238,208 B2 | 7/2007 | Camino et al. |
| 7,250,550 B2 | 7/2007 | Overby et al. |
| 7,297,163 B2 | 11/2007 | Huebner |
| 7,309,360 B2 | 12/2007 | Tornier et al. |
| 7,329,284 B2 | 2/2008 | Maroney et al. |
| 7,338,498 B2 | 3/2008 | Long et al. |
| 7,338,528 B2 | 3/2008 | Stone et al. |
| 7,462,197 B2 | 12/2008 | Tornier et al. |
| 7,520,898 B2 | 4/2009 | Re et al. |
| 7,604,637 B2 | 10/2009 | Johnson et al. |
| 8,062,376 B2 | 11/2011 | Shultz et al. |
| 8,414,586 B2 | 4/2013 | Cawthan et al. |
| 8,864,834 B2 | 10/2014 | Boileau et al. |
| 8,974,536 B2 | 3/2015 | Walch et al. |
| 9,089,435 B2 | 7/2015 | Walch et al. |
| 9,408,652 B2 | 8/2016 | Hassler et al. |
| 2001/0032021 A1 | 10/2001 | McKinnon |
| 2001/0047210 A1 | 11/2001 | Wolf |
| 2001/0049561 A1 | 12/2001 | Dews et al. |
| 2002/0032484 A1 | 3/2002 | Hyde |
| 2002/0099381 A1 | 7/2002 | Maroney |
| 2002/0138148 A1 | 9/2002 | Hyde |
| 2002/0143402 A1 | 10/2002 | Steinberg |
| 2002/0151982 A1 | 10/2002 | Masini |
| 2002/0177901 A1 | 11/2002 | Howie |
| 2003/0009171 A1 | 1/2003 | Tornier |
| 2003/0065397 A1 | 4/2003 | Hanssen et al. |
| 2003/0097183 A1 | 5/2003 | Rauscher et al. |
| 2003/0114933 A1 | 6/2003 | Bouttens et al. |
| 2003/0125809 A1* | 7/2003 | Iannotti ............ A61B 17/1684 623/19.13 |
| 2003/0149485 A1 | 8/2003 | Tornier |
| 2003/0158605 A1 | 8/2003 | Tornier |
| 2003/0181916 A1 | 9/2003 | Wolford |
| 2004/0002765 A1 | 1/2004 | Maroney et al. |
| 2004/0006392 A1 | 1/2004 | Grusin et al. |
| 2004/0030394 A1 | 2/2004 | Horber |
| 2004/0034431 A1 | 2/2004 | Maroney et al. |
| 2004/0064189 A1 | 4/2004 | Maroney et al. |
| 2004/0064190 A1 | 4/2004 | Ball et al. |
| 2004/0068320 A1 | 4/2004 | Robie et al. |
| 2004/0133276 A1 | 7/2004 | Lang et al. |
| 2004/0138754 A1 | 7/2004 | Lang et al. |
| 2004/0148033 A1 | 7/2004 | Schroeder |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0210317 A1 | 10/2004 | Maroney et al. |
| 2004/0220673 A1 | 11/2004 | Pria |
| 2004/0220674 A1 | 11/2004 | Pria |
| 2004/0225367 A1 | 11/2004 | Glien et al. |
| 2004/0230197 A1 | 11/2004 | Tornier et al. |
| 2004/0249383 A1 | 12/2004 | White et al. |
| 2004/0267370 A1 | 12/2004 | Ondrla |
| 2005/0008672 A1 | 1/2005 | Winterbottom et al. |
| 2005/0010304 A1 | 1/2005 | Jamali |
| 2005/0015154 A1 | 1/2005 | Lindsey et al. |
| 2005/0033443 A1 | 2/2005 | Blatter et al. |
| 2005/0043805 A1 | 2/2005 | Chudik |
| 2005/0049709 A1 | 3/2005 | Tornier |
| 2005/0060039 A1 | 3/2005 | Cyprien |
| 2005/0065612 A1 | 3/2005 | Winslow |
| 2005/0085919 A1 | 4/2005 | Durand Allen et al. |
| 2005/0085921 A1 | 4/2005 | Gupta et al. |
| 2005/0090902 A1 | 4/2005 | Masini |
| 2005/0107882 A1 | 5/2005 | Stone et al. |
| 2005/0113837 A1 | 5/2005 | Salyer |
| 2005/0113931 A1 | 5/2005 | Horber |
| 2005/0119531 A1 | 6/2005 | Sharratt |
| 2005/0143818 A1 | 6/2005 | Yuan et al. |
| 2005/0143829 A1 | 6/2005 | Ondrla et al. |
| 2005/0159751 A1 | 7/2005 | Berthusen et al. |
| 2005/0165490 A1 | 7/2005 | Tornier |
| 2005/0177241 A1 | 8/2005 | Angibaud et al. |
| 2005/0186247 A1 | 8/2005 | Hunter et al. |
| 2005/0197708 A1 | 9/2005 | Stone et al. |
| 2005/0209700 A1 | 9/2005 | Rockwood et al. |
| 2005/0216092 A1 | 9/2005 | Marik et al. |
| 2005/0240267 A1 | 10/2005 | Randall et al. |
| 2005/0245934 A1 | 11/2005 | Tuke et al. |
| 2005/0251263 A1 | 11/2005 | Forrer et al. |
| 2005/0256584 A1 | 11/2005 | Farrar |
| 2005/0267590 A1 | 12/2005 | Lee |
| 2005/0278030 A1 | 12/2005 | Tornier et al. |
| 2005/0278031 A1 | 12/2005 | Tornier et al. |
| 2005/0278032 A1 | 12/2005 | Tornier et al. |
| 2005/0278033 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0009852 A1 | 1/2006 | Winslow et al. |
| 2006/0020344 A1 | 1/2006 | Shultz et al. |
| 2006/0025796 A1 | 2/2006 | Merced O'Neill |
| 2006/0030946 A1 | 2/2006 | Ball et al. |
| 2006/0111787 A1 | 5/2006 | Bailie et al. |
| 2006/0122705 A1 | 6/2006 | Morgan |
| 2006/0195110 A1 | 8/2006 | White et al. |
| 2006/0241775 A1 | 10/2006 | Buss |
| 2007/0078516 A1 | 4/2007 | Emami |

(56) References Cited

U.S. PATENT DOCUMENTS

| | | | |
|---|---|---|---|
| 2007/0142916 | A1 | 6/2007 | Olson, Jr. et al. |
| 2007/0156250 | A1 | 7/2007 | Seitz et al. |
| 2007/0173945 | A1 | 7/2007 | Wiley et al. |
| 2007/0179562 | A1 | 8/2007 | Nycz |
| 2007/0198087 | A1 | 8/2007 | Coleman et al. |
| 2007/0225817 | A1 | 9/2007 | Reubelt et al. |
| 2007/0225818 | A1 | 9/2007 | Reubelt et al. |
| 2007/0225821 | A1 | 9/2007 | Reubelt et al. |
| 2007/0244564 | A1 | 10/2007 | Ferrand et al. |
| 2007/0250174 | A1 | 10/2007 | Tornier et al. |
| 2007/0276509 | A1 | 11/2007 | Ratcliffe et al. |
| 2009/0125113 | A1 | 5/2009 | Guederian et al. |
| 2009/0270993 | A1 | 10/2009 | Maisonneuve et al. |
| 2009/0287309 | A1 | 11/2009 | Walch et al. |
| 2009/0292364 | A1 | 11/2009 | Linares |
| 2009/0306782 | A1 | 12/2009 | Schwyzer |
| 2010/0280517 | A1 | 11/2010 | Cawthan et al. |
| 2010/0280518 | A1 | 11/2010 | Gary |
| 2011/0098822 | A1 | 4/2011 | Walch et al. |
| 2011/0166661 | A1 | 7/2011 | Boileau et al. |
| 2011/0213372 | A1 | 9/2011 | Keefer et al. |
| 2011/0264153 | A1 | 10/2011 | Hassler et al. |
| 2014/0058523 | A1 | 2/2014 | Walch et al. |
| 2015/0012104 | A1 | 1/2015 | Boileau et al. |
| 2015/0297354 | A1 | 10/2015 | Walch et al. |
| 2016/0331555 | A1 | 11/2016 | Hassler et al. |

FOREIGN PATENT DOCUMENTS

| | | |
|---|---|---|
| DE | 1950937 | 9/1996 |
| DE | 19630298 | 1/1998 |
| EP | 0257359 | 11/1991 |
| EP | 0299889 | 3/1992 |
| EP | 0524857 | 1/1993 |
| EP | 0549480 | 6/1993 |
| EP | 0617934 | 10/1994 |
| EP | 0679375 | 11/1995 |
| EP | 0712617 | 5/1996 |
| EP | 0715836 | 6/1996 |
| EP | 0599429 | 10/1997 |
| EP | 0797964 | 10/1997 |
| EP | 0864306 | 9/1998 |
| EP | 0903128 | 3/1999 |
| EP | 1062923 | 12/2000 |
| EP | 1064890 | 1/2001 |
| EP | 0664108 | 8/2002 |
| EP | 0809986 | 10/2002 |
| EP | 0927548 | 5/2003 |
| EP | 1323395 | 7/2003 |
| EP | 0807426 | 10/2003 |
| EP | 1380274 | 1/2004 |
| EP | 1402853 | 3/2004 |
| EP | 1477120 | 11/2004 |
| EP | 1195149 | 7/2005 |
| EP | 1570816 | 9/2005 |
| EP | 1607069 | 12/2005 |
| EP | 1652482 | 5/2006 |
| EP | 0903127 | 6/2007 |
| EP | 1952788 | 1/2008 |
| EP | 1952771 | 8/2008 |
| EP | 1952788 | 8/2008 |
| EP | 1402854 | 7/2010 |
| EP | 1952771 | 10/2016 |
| EP | 3335676 | 6/2018 |
| FR | 2216981 | 9/1974 |
| FR | 2248820 | 5/1975 |
| FR | 2545352 | 11/1984 |
| FR | 2574283 | 6/1986 |
| FR | 2652498 | 4/1991 |
| FR | 2664809 | 1/1992 |
| FR | 2699400 | 6/1994 |
| FR | 2704747 | 11/1994 |
| FR | 2721200 | 12/1995 |
| FR | 2726994 | 5/1996 |
| FR | 2737107 | 1/1997 |
| FR | 2835425 | 8/2003 |
| FR | 2836039 | 8/2003 |
| SU | 749392 | 7/1980 |
| WO | WO 1991/007932 | 6/1991 |
| WO | WO 1993/009733 | 5/1993 |
| WO | WO 1996/017553 | 6/1996 |
| WO | WO 1998/046172 | 10/1998 |
| WO | WO 1999/049792 | 10/1999 |
| WO | WO 1999/065413 | 12/1999 |
| WO | WO 2000/015154 | 3/2000 |
| WO | WO 2000/041653 | 7/2000 |
| WO | WO 2000/062718 | 10/2000 |
| WO | WO 2001/047442 | 7/2001 |
| WO | WO 2002/039931 | 5/2002 |
| WO | WO 2002/039933 | 5/2002 |
| WO | WO 2002/049516 | 6/2002 |
| WO | WO 2002/067821 | 9/2002 |
| WO | WO 2003/005933 | 1/2003 |
| WO | WO 2003/092513 | 11/2003 |
| WO | WO 2003/094806 | 11/2003 |
| WO | WO 2006/039483 | 4/2006 |
| WO | WO 2007/109340 | 9/2007 |
| WO | WO 2007/109291 | 4/2008 |
| WO | WO 2007/109319 | 6/2008 |

OTHER PUBLICATIONS

"Aequalis-Fracture Suture Technique in 5 Steps," Tornier, Inc., in 2 pages.
"Aequalis-Glenoid Keeled and Pegged—Surgical Technique," Tornier, Inc., in 12 pages.
"Aequalis Press-Fit Shoulder Prosthesis—Surgical Technique," Tornier, Inc., in 27 pages.
"Aequalis Resurfacing Head", retrieved from http://www/tornier-us.com/upper/shoulder/shorec004/index.php?pop+1 on Apr. 14, 2010.
"Aequalis-Reversed™ Shoulder Prosthesis, Surgical Technique," Tornier, Inc., in 24 pages.
"Anatomic Glenoid, Surgical Technique," Smith & Nephew; Inc., Feb. 2000 in 6 pages.
"Anatomical Shoulder™—Cemented Shoulder Prosthesis Product Information and Surgical Technique," Sulzer Medica, 2000, in 30 pages.
"Anatomical Shoulder™ System—The new removable head option," Zimmer Inc., 2004 in 6 pages.
"Anatomical Shoulder™ System Surgical Technique—Removable head option for improved surgical results," Zimmer, Inc, 2004 in 33 pages.
Apoil, A., "A Condyle for the Rotator Cuff Muscles: The Total Shoulder Prosthesis," Aesculap—ICP S.A., Feb. 1994, in 4 pages.
Bigliani/Flatow®—The Complete Shoulder Solution, Designed ;Shoulder Surgery, Zimmer, Inc., 2001 in 6 pages.
Bigliani/Flatow®—The Complete Shoulder Solution, Total Shoulder Arthoroplasty Surgical Technique, Zimmer, Inc., 2003, in 30 pages.
Bigliani/Flatow®—The Complete Shoulder Solution, 4-Part Fracture of the Humerus Surgical Technique, Zimmer, Inc., 2001.
"Bio-Modular® / Bi-Polar Shoulder Arthroplasty," Biomet, Inc., 1997, in 2 pages.
"Bio-Modular® Choice—Shoulder System—Surgical Technique," Biomet Orthopedics, Inc., 2004, in 16 pages.
"Bio-Modular Total Shoulder Surgical Technique," Biomet Orthopedics, Inc., 2001.
Boileau, P., et al. "Adaptability and modularity of shoulder prosthese," Maitrise Orthopédique, https://www.maitriseorthop.com/corpusmaitri/orthopaedic/prothese_epaule_orthop/boileau_us.shtml, downloaded Jan. 3, 2006.
Boileau, P., et al. "Arthroscopic Repair of Full-Thickness Tears of the Supraspinatus: Does the Tendon Really Heal?" The Journal of Bone and Joint Surgery, Inc., Jun. 2005, 87A(6): 1229-1240.
Buechel, F F., "Buechel-Pappas™ Modular Salvage Shoulder System, Surgical Procedure," Endotec, Inc., Aug. 2001, in 8 pages.
Buechel, F.F., "Buechel-Pappas™ Resurfacing Shoulder System, Surgical Procedure" Endotec, Inc., Aug. 2000, in 8 pages.

(56) References Cited

OTHER PUBLICATIONS

Buechel, F.F., "Buechel-Pappas™ Total Shoulder System, Surgical Procedure," Endotec, Inc., Aug. 2000, in 16 pages.
Cofield, R.H., "Cofield$^2$ Total Shoulder System, Surgical Technique," Smith & Nephew, 1997 in 32 pages.
"Copeland™ Humeral Resurfacing Head," Biomet Orthopedics, Inc., 2001, in 12 pages.
"Delta CTA™ Reverse Shoulder Prosthesis—Surgical Technique," DePuy International Ltd., revised Aug. 2004, in 28 pages.
"Design Rationale," Latitude® Total Elbow, pp. 3-38.
Fenlin, Jr., J.M., "Total Glenohumeral Joint Replacement," Symposium on Surgery of the Shoulder, Orthopedic Clinics of North America, Apr. 1975, 6(2): 565-583.
"Global C.A.P. ™ Surgical Technique, Resurfacing Humeral Head Implant," DePuy International, Ltd., revised Oct. 2004, in 23 pages.
Hertel, R., "Technical considerations for implantation of EPOCA glenoid components (Leseprobe)," Epoca Newsletter, May 14, 2001, in 1 page.
Klein, T.J., et al., "Mechanically Favorable Bone Remodeling in Rotator Cuff Arthropathy Patients with Good Function," Minneapolis Sports Medicine Center and University of Minnesota, in 2 pages.
Mansat, M., "Neer 3™, Surgical Technique for Fractures," Smith & Nephew, Sep. 2000, in 19 pages.
Nicholson, G.P., "Chapter 7, Arthroplasty and Rotator Cuff Deficiency," Shoulder Arthroplastry, 2005, pp. 149-166.
Office Communication for European Appl. No. 08356017.7 dated May 26, 2015 in 16 pages.
Office Communication for European Appl. No. 08356018.5 dated Mar. 16, 2015 in 5 pages.
Office Communication for European Appl. No. 08356018.5 dated Dec. 1, 2015 in 3 pages.
"Offset Head: Bio-Modular® Total Shoulder," Biomet, Inc. 2000 in 2 pages.
Search Report for European Appl. No. 08356017.7 dated Jun. 4, 2008 in 5 pages.
Search Report for European Appl. No. 08356018.5 dated Jun. 16 2008 in 6 pages.
"The FOUNDATION® Total Shoulder System," Encore Surgical, in 2 pages.
"The Townley Modular Shoulder—Design by Reason," Biopro, Inc., in 2 pages.
"TORNIER Surgical Technique Addendum, Tornier Aequalis® Reversed Hemi-Adaptor Technique," Tornier, Inc., Aug. 8, 2005.
"TORNIER Surgical Technique Addendum, Aequalis® Reversed Shoulder Polyethylene Insert," Tornier, Inc., Oct. 8, 2005, in 1 page.
"Zimmer® Shoulder Retractors," Zimmer, Inc., 2000, in 2 pages.
Search Report for European Appl. No. 18153967.7 dated May 22, 2018 in 6 pages.

* cited by examiner

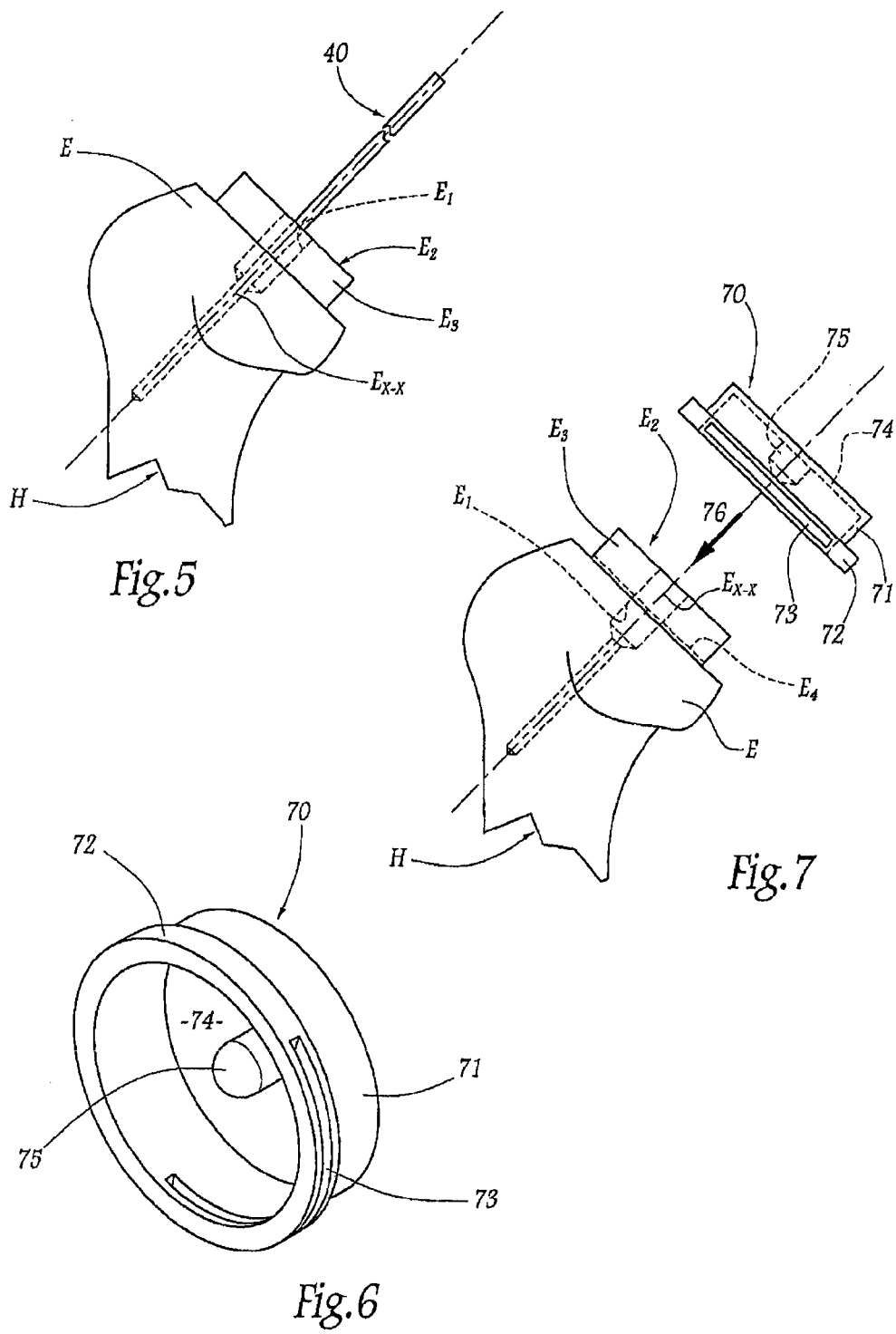

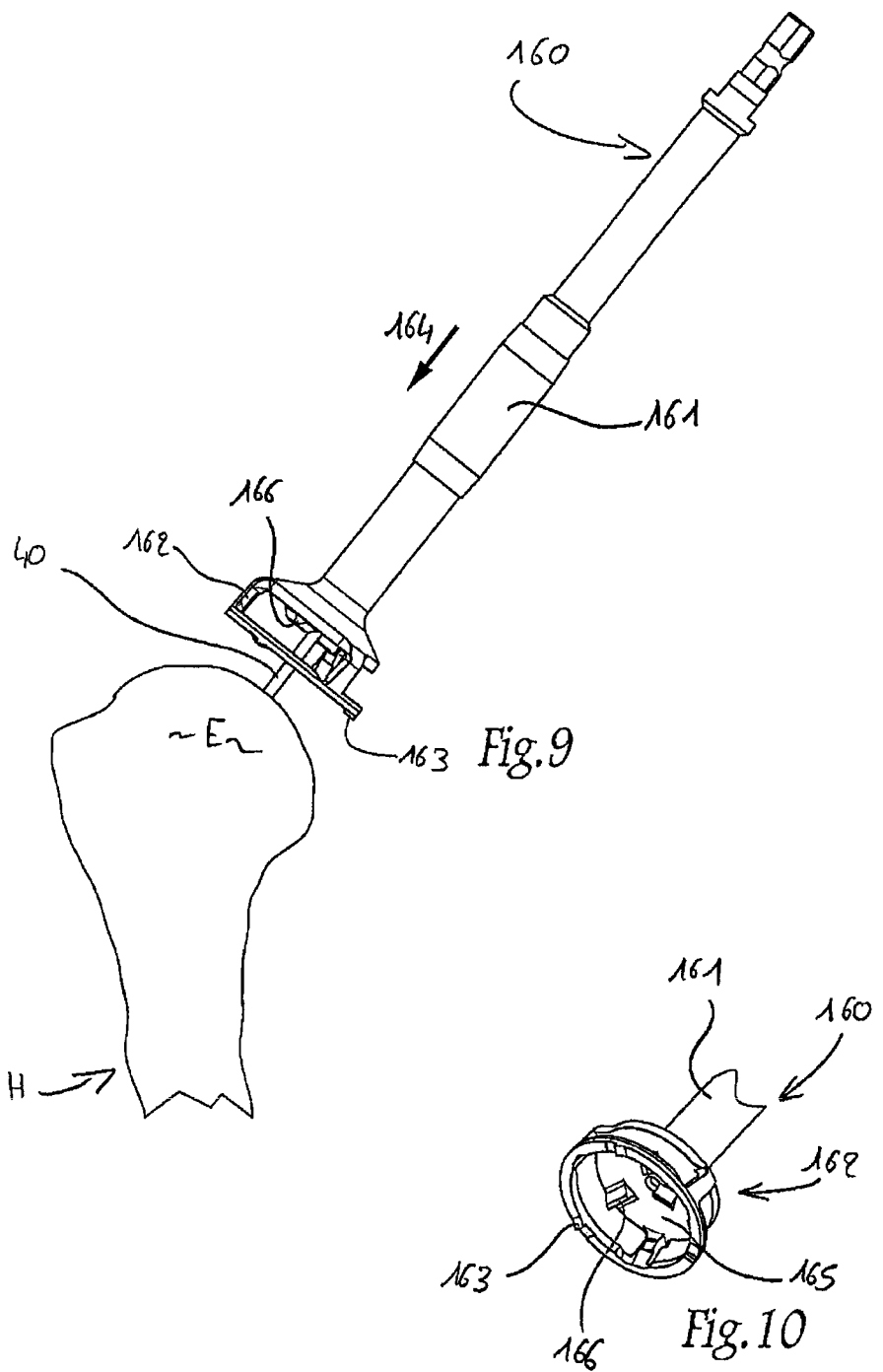

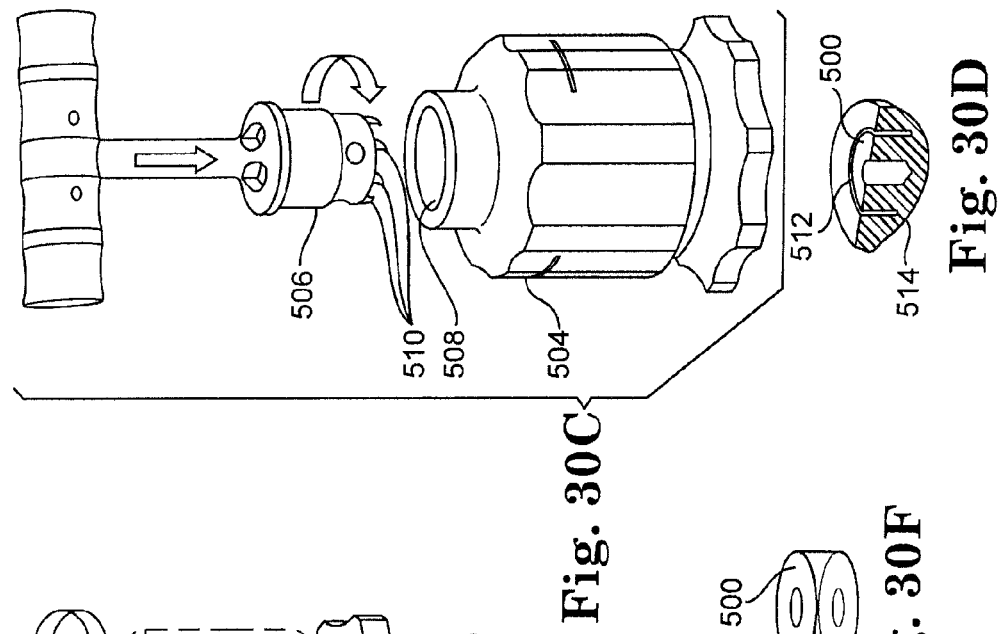
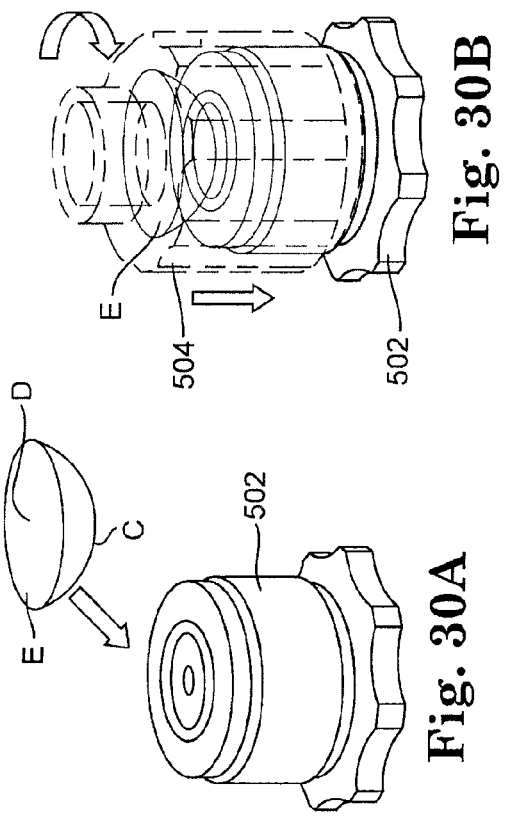
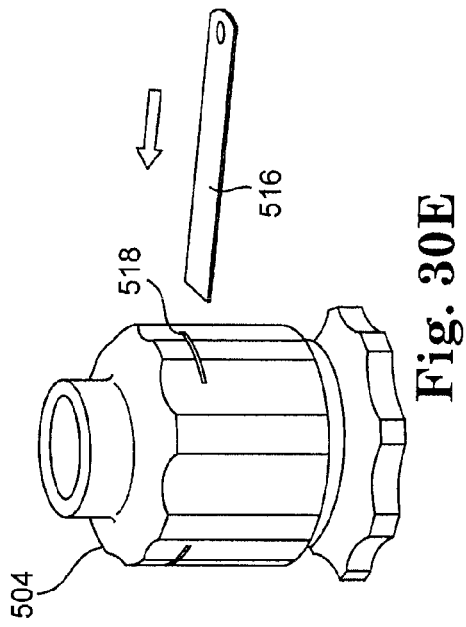

METHOD AND APPARATUS FOR FITTING A SHOULDER PROSTHESIS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The present invention relates to a method and apparatus for the preparation and implantation of a bone graft to lateralize the glenoid component of an inverted or an anatomical shoulder prosthesis.

BACKGROUND OF THE INVENTION

In the field of total shoulder prostheses, prostheses are commonly said to be inverted when they comprise, on the one hand, a glenoid part integral with the glenoid surface of a scapula of a patient's shoulder and delimiting a convex articular surface and, on the other hand, a humeral part integral with the humerus of the shoulder and delimiting a concave articular surface, the cooperation of these articular surfaces allowing an articulated connection to be reproduced at the shoulder. With this type of prosthesis, it is common, during adduction movement of the shoulder, for the lower portion of the humeral prosthetic part to strike the pillar of the scapula, i.e. the lower portion of the bone glenoid surface located, when the patient stands upright, just below the glenoid prosthetic part. This interference between the humeral prosthetic part and the scapula limits the range of the adduction movement and may cause pain to the patient or even lead to the prosthesis becoming dislodged, in particular by osteolysis of the scapula.

BRIEF SUMMARY OF THE INVENTION

The present invention is directed to a surgical method and a corresponding set of surgical instruments allowing the risks of interference between the scapula and the humeral part of an inverted or an anatomical shoulder prosthesis to be limited without having recourse to complex configurations of this prosthesis and, indeed, using for the most part existing inverted prostheses. All references to a shoulder prosthesis should be interpreted to include a total shoulder prosthesis with a humeral component and a glenoid component (including anatomical, inverted, or interpositional configurations), or a partial shoulder prosthesis with a glenoid component with an anatomical or resurface humeral head.

One embodiment of this invention relates to a surgical method for fitting an inverted shoulder prosthesis, the prosthesis including a glenoid component having a convex articular surface and an opposing face, this fitting method including successive preoperative steps in which:
i) there is provided a bone graft,
ii) the graft is placed on the previously prepared glenoid surface of a scapula of a patient's shoulder, and
iii) the glenoid component is implanted so as to cover the graft positioned on the glenoid surface with the opposing face of the glenoid component and to anchor the glenoid component in the glenoid surface through the graft.

Thus, the basic idea of the invention is to "lateralize" the glenoid component relative to the patient's scapula, i.e. to withdraw it from the patient's scapula in a plane frontal to this patient, by interposing the bone graft between this glenoid component and the glenoid surface. In other words, this bone graft forms an outer lateral extension of the glenoid surface, extending the scapula, whereas the combination of this graft and the prosthetic glenoid component forms a composite prosthetic unit. It will be understood that a glenoid component of a current prosthesis, of which the design has been tried and tested, can thus be implanted so as to cover the side of the graft opposing the glenoid surface, wherein it will be noted that, for purposes of secure fixing, this component must have bone anchoring structure, such as a central tail, sufficiently elongate to pass straight through the graft and be secured in the bone of the scapula delimiting the glenoid surface. Once the bone graft has fused with the glenoid surface, the distal surface of the bone graft becomes the effective glenoid surface. References to glenoid surface should be interpreted to include a prepare or an unprepared exposed surface of a glenoid cavity.

As the articular face of the glenoid component occupies, relative to the scapula, a position laterally more remote than the position that this face would occupy were the graft omitted, there is a significantly reduced risk of interference between the pillar of the scapula and the lower portion of the humeral prosthetic part cooperating with the glenoid articular face. The lateralization of the prosthetic glenoid component also leads to an increase in the tension in the rotator muscles of the shoulder and an increase in the co-adaptation vector of the deltoid muscle. The prosthetic glenoid and humeral components are thereby stabilized and thus benefit from better mobility in relative rotation, without running the risk of dislocation of the shoulder.

In the preferred embodiment, the geometric centre of articulation of the prosthesis is situated at the bone face in the glenoid surface. The radius of curvature of convex articular surface of the glenoid component is preferably selected so the center of rotation is in or behind a plane comprising distal surface of the bone graft.

Furthermore, compared to an inverted shoulder prosthesis from the prior art and which can thus be described as a "medialized prosthesis", the "lateralized" prosthesis according to the invention restores some of the curved surface of the patient's shoulder, thus giving it a more pleasing appearance than the "coat hanger" appearance conferred by medialized prostheses.

The surgical method according to the invention is simple, quick, easy and reproducible. In practice it has the advantage of not having to completely expose the patient's glenoid surface, exposure actually being able to be limited to the positioning of the graft. In the preferred embodiment, the bone graft is taken from the patient so as to minimize the risk of contamination, although allografts, xenografts, natural or synthetic materials may be used.

According to a particularly advantageous implementation of the method according to the invention, in order to provide the bone graft in preferably taken from the upper epiphysis of the humerus of the patient's shoulder. In this way, the graft used originates from the patient, and this limits the risk of rejection, poor biological compatibility, transmission of disease or infection. Furthermore, advantageous use is made of the fact that, in order to implant the humeral prosthetic part, it is necessary to prepare the epiphysis of the patient's humerus, by withdrawing a substantial part of the cancellous bone matter forming this epiphysis which, in accordance with this aspect of the invention, can be used to provide the graft whereas, up until now, this matter was scrapped.

In practice, the method includes a shaping step in which the bone matter forming the upper humeral epiphysis is shaped into a one-piece volume extending in length about an axis inclined relative to the longitudinal direction of the humerus, and a cutting step in which the volume of bone matter is removed from the humerus by cutting the humeral epiphysis transversely to the axis of this volume, the volume of bone matter thus removed forming the graft.

The present method may include one or more of the following steps:
- the length of the graft is adjusted along the axis of the volume of bone matter;
- the longitudinal end faces of the graft are respectively shaped to be substantially complementary to said opposing face of the glenoid component and the glenoid surface previously prepared;
- during the shaping step, the shaped volume of bone matter is chosen from a cylinder and a frustum of a cone, centered on the axis of this volume;
- before or during the shaping step, the end of the upper humeral epiphysis is resected;
- the upper humeral epiphysis is resected over a first plane and in which, during the cutting step, the humeral epiphysis is cut over a second plane, said first and second plane being transverse to the axis of the volume of bone matter;
- the relative inclination of said first and second planes is adjusted;
- during or after the shaping step, a recess centered on the axis of the volume of bone matter is dug in the humeral epiphysis, and in which, during the step, the glenoid component is anchored in the glenoid surface through this recess;
- before carrying out the shaping step, there is inserted into the humeral epiphysis a marker pin allowing, during the shaping step, positioning of the axis of the volume of bone matter relative to the humerus.

In accordance with another possibility according to the invention, rather than taking the bone graft from the patient's humeral epiphysis, the bone graft provided in step i) is chosen from a graft taken from a bone region in the patient other than the upper humeral epiphysis, in particular from the patient's ilium, an allograft and a graft of synthetic origin.

In accordance with an option of the method according to the invention that can be used equally well with a graft taken from the humeral epiphysis or elsewhere and with an allograft or else a graft of synthetic origin, during step ii), a protection layer is attached to at least a part of the graft that is not in contact with the glenoid surface, and, during step iii), at least a part of the opposing face of the glenoid component is supported on the protection layer.

In one embodiment, some or all of the surfaces on the glenoid component that engage with the bone graft are covered with hydroxyapatite or materials having a functionally similar surface state, such as a honeycomb surface state, allowing bone adhesion and rehabilitation to be improved. Selected surface of the glenoid component may be constructed of materials that facilitate fusion with bone, such as disclosed in U.S. Pat. No. 7,250,550.

According to yet another possibility of the invention, the bone graft provided in step i) consists of a purée of bone substance, it being appreciated that this bone substance can originate either from the patient, in particular from the upper epiphysis of his humerus, or from another, possibly synthetic, source. This purée of bone substance is advantageously used with a structure of protection as defined hereinbefore, which comprises a lattice shaped into a cage filled with the purée. This lattice cage allows good exchange of biological flows between the purée forming the graft and the surrounding tissues of the shoulder.

The invention also relates to a set of surgical instruments for fitting a shoulder prosthesis. The set includes a shaping ancillary instrument that shapes the bone matter forming the upper humeral epiphysis of a humerus into a one-piece volume extending in length about an axis inclined relative to the longitudinal direction of the humerus, and a cutting ancillary instrument that cuts the humeral epiphysis shaped by the shaping ancillary instrument, for cutting the volume of bone matter transversely to the axis of this volume. The cutting ancillary instrument thus allowing the volume of bone matter to be removed from the humerus so that said volume forms a graft.

The set of instruments according to the invention allows implementation of the fitting method defined hereinbefore, the shaping and cutting steps of which are respectively carried out by the shaping and cutting ancillary instrument. The volume of bone matter removed from the humerus using the cutting ancillary instrument can thus be used as the bone graft for carrying out the general fitting method defined hereinbefore in order laterally to offset the convex articular surface of a glenoid component of the prosthesis relative to the scapula of the patient's shoulder, during implantation of this glenoid component.

According to advantageous features of this set of instruments, taken in isolation or in any technically feasible combination:
- it comprises resecting instrument for resecting the end of the humeral epiphysis, which resecting instrument are either carried by a specific resection ancillary instrument, distinct from the other ancillary instrument of the set or integrated in the shaping ancillary instrument;
- the resecting instrument comprises a planar reamer so as to resect the humeral epiphysis over a first plane transverse to the axis of the volume of bone matter;
- it comprises humeral epiphysis drilling instrument which are adapted to form a recess, centered on the axis of the volume of bone matter, in the humeral epiphysis and which are either integrated in the shaping ancillary instrument or the resection ancillary instrument or are carried by a specific drilling ancillary instrument distinct from the other ancillary instrument of the set;
- it further comprises a marker pin or a similar marker instrument capable of being inserted into the humeral epiphysis and suitable for guiding the shaping ancillary instrument and optionally at least one of the other ancillary instrument of the set;
- it further comprises an inserting ancillary instrument for inserting the marker pin into the humeral epiphysis, which inserting instrument is suitable for adjusting the direction of insertion of this pin relative to the humerus;
- the inserting ancillary instrument comprises, on the one hand, a rounded bell-shaped body configured internally to cover the upper humeral epiphysis in the manner of a cap and, on the other hand, a guide for applying the marker pin, which guide opens into the body;
- the shaping ancillary instrument comprises a bell-shaped saw which is suitable for cutting the bone matter forming the humeral epiphysis by shaping it into said volume of bone matter
- the saw has an optionally perforated cylindrical or frustoconical inner face so as to provide the volume of bone matter with the overall shape of a cylinder or frustum of a cone, centered on the axis of this volume;

the cutting ancillary instrument comprises a tubular block suitable for being slipped about the volume of bone mass shaped by the shaping ancillary instrument, this block delimiting, at its longitudinal end turned during operation toward the humerus, an incision zone in the humeral epiphysis, in order to cut the volume of bone matter transversely to the axis thereof;

the incision zone forms a transverse slot for the passage of a saw blade or the like, in order to cut the volume of bone matter over a second plane transverse to the axis of this volume;

the cutting ancillary instrument comprises an annular body adapted to be mounted round the humeral epiphysis while surrounding at least the volume of bone matter shaped by the shaping ancillary instrument, this body delimiting a guide surface for a cutting instrument to cut at least the volume of bone matter transversely to its axis.

The invention also relates to an inverted shoulder prosthesis comprising a glenoid component having a convex articular surface and an opposing face, wherein said prosthesis comprises a protection layer for protecting a bone graft interposed, when the prosthesis is fitted, between said opposing face and the glenoid surface of a scapula of a patient's shoulder, this protection layer being suitable for both covering at least a part of the graft that is not in contact with the glenoid surface and forming a support for at least a part of said opposing face.

The graft protected by the protection layer of the prosthesis according to the invention can be taken from the upper humeral epiphysis using the set of instruments defined hereinbefore, or else be chosen from a graft taken from a bone region in the patient other than the upper humeral epiphysis, in particular from the patient's ilium, an allograft and a graft of synthetic origin. In practice, this prosthesis is fitted in accordance with the general method defined hereinbefore.

According to advantageous features of this prosthesis optionally includes a protection layer, such as for example, a layer of hydroxyapatite or other material that has a functionally similar surface state, such as a honeycomb surface state, allowing bone adhesion and rehabilitation to be improved. In another embodiment, the protection layer includes a shape of a ring suitable for surrounding, in a close-fitting manner, the portion of the bone graft not in contact with the glenoid surface, it being appreciated that, in practice, this ring is used for a one-piece graft obtained, in particular, by the set of instruments as defined hereinbefore. The protection layer may also be a lattice shaped as a cage adapted to be filled with a purée of bone matter forming the graft.

BRIEF DESCRIPTION OF THE SEVERAL VIEWS OF THE DRAWINGS

A better understanding of the invention will be facilitated on reading the following description given merely by way of example and with reference to the drawings, in which:

FIG. 5 is a view similar to FIG. 2, illustrating the humerus after use of the ancillary instrument of FIGS. 3 and 4;

FIG. 6 is a schematic perspective view of another ancillary instrument pertaining to the set of instruments;

FIG. 7 is a view similar to FIG. 2, illustrating the application of the ancillary instrument of FIG. 6 to the humerus after use of the ancillary instrument of FIG. 4;

FIGS. 8 to 12 show a second embodiment of a set of instruments according to the invention, FIGS. 8, 9, 11 and 12 being similar respective schematic elevations of four ancillary instruments pertaining to this set and used in succession, to fit the prosthesis from FIG. 1, whereas FIG. 10 is a partial perspective view of the ancillary instruments from FIG. 9, shown alone;

FIGS. 30A-30F illustrate a method and tool set for preparing a bone graft in accordance with an embodiment of the present invention.

DETAILED DESCRIPTION OF THE INVENTION

Figure 1:
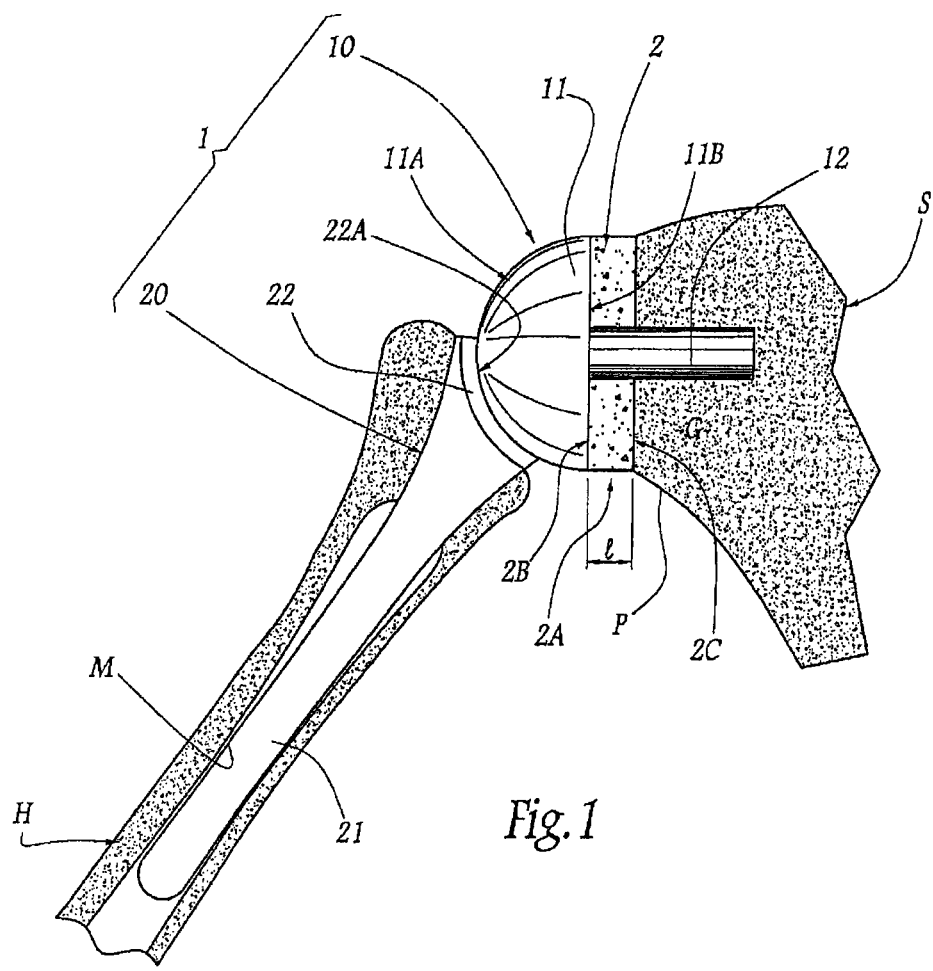
FIG. 1 is a basic schematic illustration of an inverted shoulder prosthesis, implanted at a patient's shoulder.

FIG. 1 shows a shoulder prosthesis 1 comprising a glenoid component 10 and a humeral component 20, respectively implanted in the scapula S and the humerus H of a patient's shoulder. The glenoid components shown herein are illustrated schematically. The method and apparatus of the various embodiments disclosed herein may be used with a variety of other glenoid components, such as for example those disclosed in U.S. Pat. Nos. 7,033,396; 6,953,478; 6,761,740; 6,626,946; 5,702,447 and U.S. Publication Nos. 2004/0220673; 2005/0278030; 2005/0278031; 2005/0278032; 2006/0020344, which are hereby incorporated by reference.

The glenoid component 10 comprises a head 11 which has, on the side opposing the glenoid surface G of the scapula S, a convex articular surface 11A of generally hemispherical shape and, on the side turned toward the glenoid surface, an opposing face 11B. In the example considered in the FIGS., this face 11B is generally planar but, in non-illustrated variations, this face 11B can have a more elaborate geometry, being, for example, substantially concave or convex.

The glenoid component 10 also comprises an anchoring tail 12 which extends transversely so as to protrude from the face 11B, in the direction opposing the face 11A, and the free end part of which is securely anchored in the glenoid surface G, thus joining the glenoid component to the scapula S. In practice, in a manner not shown, the anchoring tail 12 can be provided, at its end turned toward the head 11, with a base accommodated inside the head 11, being securely joined thereto. In other words, more generally, the connection between the tail 12 and the head 11 can assume a broad range of forms, such as material continuity, respective wedging surfaces, attached mechanical assembly structures, etc. Also by way of non-illustrated variation, the tail 12 can be externally threaded or, generally, have a surface state promoting the anchoring thereof.

Between the face 11B of the glenoid head 11 and the glenoid surface G of the scapula S there is interposed a bone graft 2 having a substantially cylindrical outer shape with a circular base, the external diameter of which is substantially equal to that of the head 11. The outer lateral face 2A of the graft 2 thus extends substantially in the extension of the hemispherical face 11A. The graft 2 has, on its side opposing the glenoid surface G, a longitudinal end face or distal surface 2B covered by the face 11B of the head 11 and, on its side directed toward the glenoid surface, a longitudinal end face or medial surface 2C resting against the glenoid surface G. Once the bone graft 2 fuses with the glenoid surface G, the effective glenoid surface is displaced laterally outward to the distal surface 2B of the bone graft 2.

In the example considered in the FIGS., the longitudinal end faces 2B and 2C are planar; this has proven to be an embodiment that is simple to handle and easy to obtain, as will be referred to hereinafter. However, in practice, these faces 2B and 2C can have more elaborate geometries: on one side, the face 2B is provided to be covered in a substantially complementary manner with the face 11B of the head 11, including in this face the zones or the structure for connecting to the tail 12, it being understood that, as indicated hereinbefore, this face 11B can be generally concave, convex or planar; on the opposing side, the face 2C is provided to embrace the surface of the glenoid surface G, which has been previously prepared for this purpose, so that the face 2C and the glenoid surface are substantially complementary and can equally well be planar or curved.

The bone graft can be a one-piece bone graft, a plurality of random or pre-formed bone pieces, one or more layers of bone material, a purée of bone substance, or combinations thereof. The bone graft can be formed from the patient's bone, an allograft, a xenograft, or a combination thereof. The bone graft can optionally be resorbable. The bone graft may be used alone or in combination with bone replacements, bone fillers, bone cements and/or bone adhesives. Various bone replacements, bone fillers, bone cements and bone adhesives are disclosed in U.S. Pat. No. 6,692,563 (Zimmerman), which is hereby incorporated by reference. Various additives can be included in the bone graft, such as for example, bone growth agents or pain inhibitors. In one embodiment, reinforcing fibers are added to the purée of bone substance.

Alternatively, the bone graft can be materials into which native bone will grow to create a structure with properties comparable to native bone, such as for example, a three-dimensional porous matrix or scaffold. Examples of a porous matrix or scaffold include a reticulated bioceramic framework, structured porous tantalum, synthetic fiber mesh, and the like. Various porous matrices and scaffoldings are disclosed in U.S. Pat. Nos. 4,479,271; 6,511,511; 6,605,117; 6,797,006; 6,902,584; and 7,250,550, which are hereby incorporated by reference.

The bone graft can be made from a variety of synthetic compounds, such as for example, polyglycolide, polylactides, polycaprolactones, polytrimethylenecarbonates, polyhydroxybutyrates, polyhydroxyvalerates, polydioxanones, polyorthoesters, polycarbonates, polytyrosinecarbonates, polyorthocarbonates, polyalkylene oxalates, polyalkylene succinates, poly(malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly (amino acids), modified polysaccharides (e.g., cellulose, starch, dextran, chitin, chitosan, etc.), modified proteins (e.g., collagen, casein, fibrin, etc.) and their copolymers, or combinations thereof. Other polymers include polyglycolide, poly(L-lactide-co-glycolide), poly(D,L-lactide-co-glycolide), poly(L-lactide), poly(D,L-lactide), poly(L-lactide-co-D,L-lactide), polycaprolactone, poly(L-lactide-co-caprolactone), poly(D,L-lactide-co-caprolactone) polytrimethylenecarbonate, poly(L-lactide-co-trimethylenecarbonate), poly(D,L-lactide-co-trimethylenecarbonate), polydioxanone and copolymers, and polymer blends thereof. Various methods of manufacturing the bone graft from a synthetic compound can be found in U.S. Pat. Nos. 6,767,928; 6,730,252; 6,541,022; 6,454,811, which are hereby incorporated by reference. Optionally, before or during the surgical procedure the bone graft can be secured to the glenoid component using additional methods known in the art, such as for example biocompatible adhesives, mechanical fasteners, or combinations thereof.

The tail 12 passes straight through the graft 2, in the longitudinal direction thereof. In other words, the length of the tail is much greater than that of the graft 2, so that at least a substantial part of this tail is anchored securely in the native layer of the glenoid surface G.

In optional embodiments (not shown), the securing of the graft to the glenoid surface can be reinforced by fasteners additional to the tail 12, such as screws distributed around this tail and passing through the graft over at least part of the length thereof.

The humeral component 20 comprises a tail 21 for anchoring in the medullary cavity M of the humerus H. At its upper end, this tail is provided with a head 22 having, on its side opposing the tail 21, a concave articular face 22A in the form of a portion of a sphere, the radius of which is substantially equal to that of the face 11A. When the prosthesis 1 is implanted, as in FIG. 1, the faces 11A and 22A are in mutual surface contact, thus allowing the various desired shoulder articular movements.

Given the presence of the graft 2, the face 11A is remote from the resected surface of the glenoid surface G in the sense that, if this graft were omitted, this face 11A would be directly juxtaposed with the resected surface of the glenoid surface. Thus, on account of the graft 2, the glenoid articular face 11A and, accordingly, the humeral articular face 22A are laterally remote from the glenoid surface G, limiting the risk of the lower portion of the head 22 interfering with the bottom of the glenoid surface G, i.e. with the pillar P of the scapula S. In addition, it will be understood that, as a consequence resulting from this lateralization desired within the scope of the invention, the graft 2 acts as bone matter to make good any bone deficit in the glenoid surface.

In practice, the glenoid component 10 can be of a broad range of sizes, to which the graft 2 is adapted. Typically, the head 11 is available in at least two different sizes, namely with an external diameter of 36 mm or 42 mm, it being understood that other sizes are conceivable. Similarly, the length l of the graft 2 can have a broad range of values, distributed in practice in a uniform sequence, in a manner adapted to the morphology and/or to the pathology of the patient. The graft 2 can thus have lengths of 3, 6, 8 or 10 mm, whereas the tail 12 has a length of between 15 and 25 mm, possibly greater.

A surgical method seeking to implant the shoulder prosthesis 1 of FIG. 1 will be described hereinafter, it being understood that the prosthesis in question is merely a non-limiting illustrative example of the method and the surgical instruments used to implant this prosthesis. In other words, the method and the instruments specified hereinafter can be used to implant shoulder prostheses of a broad range of structures, of which, for example, the glenoid and/or humeral components consist of a plurality of metallic, plastic and/or ceramic-type parts joined together. Thus it is possible, for example, to use a humeral component without an anchoring tail.

Figure 2:
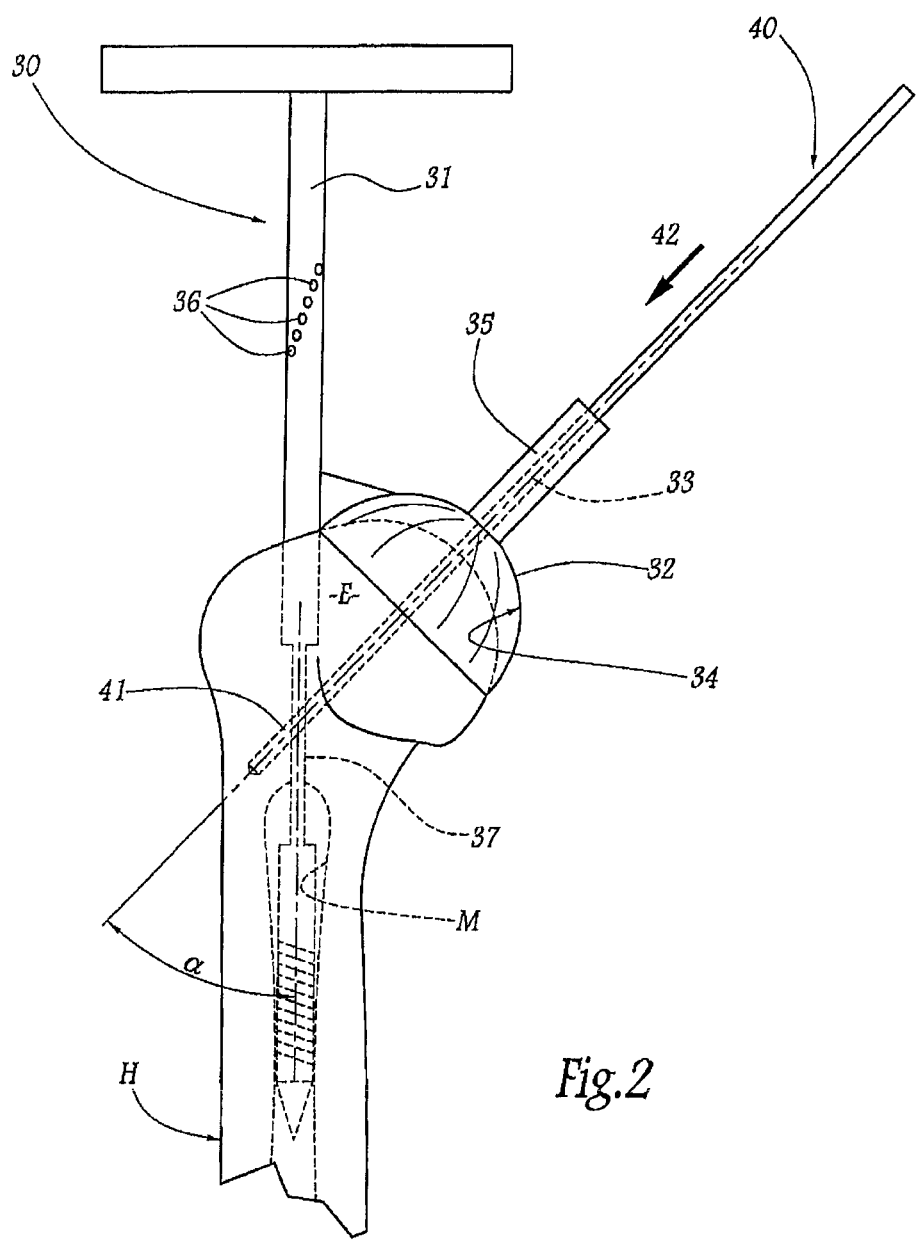
FIG. 2 is a schematic elevation of an ancillary instrument of a set of instruments according to the invention, used in order to fit the prosthesis of FIG. 1.

FIGS. 2-12 illustrate various methods and instruments for forming the bone graft in situ. In a first stage of the operation, once the soft parts of the shoulder has been removed using a deltopectoral or supero-external approach, the shaft 31 of an ancillary instruments 30 is introduced into the medullary cavity M of the humerus H, passing straight through the upper epiphysis E of the humerus H, as illustrated in FIG. 2. In order to do this, the point of entry in the humeral epiphysis is determined beforehand by radiograph analysis of the face and profile of the humerus.

In its common part, the shaft 31 is secured, in particular detachably, to a body 32 in the shape of an upwardly rounded bell. This body 32 is generally arranged transversely to the shaft 31, extending in length about a central geometrical axis 33. Projected in a plane mediolateral to the patient and containing the longitudinal axis of the shaft 31, as shown in FIG. 2, this axis 33 is inclined relative to the longitudinal axis of the shaft at an angle α of between 10 and 70°, it being noted that, spatially, the two aforementioned axes do not necessarily intersect but cross in a somewhat mutually remote manner in an anteroposterior direction.

The body 32 has on its inside a concave surface 34, of which the main center of curvature and the peak pertain substantially to the axis 33. This surface 34 is provided to reproduce approximately the surface features of the upper epiphysis of a normal anatomical humerus, it being understood that, in practice, the surgeon has a range of a plurality of homothetic ancillary instruments 30, the bodies 32 of which have respective dimensions associated with the size and the state of the patient's bones. On its outer face, the body 32 is provided with a protruding tube 35 centered on the axis 33 and opening into the interior of the body 32, on its inner surface 34.

The shaft 31 is inserted into the medullary cavity M of the humerus H until contact is established between the surface 34 and the humeral epiphysis E, the body 32 then covering the epiphysis in the manner of a cap. Then, advantageously, the shaft 31 is driven in rotation about itself, over a short course, in order to allow for the retroversion of the humerus H. In a manner known per se, the shaft 31 is provided, in its proximal end part, with diametral through-orifices 36 angularly offset from one another about the longitudinal axis of the shaft 31 and, as a function of the retroversion of the patient determined by the surgeon, an elongate rod (not shown) is introduced into one of these orifices in order effectively to display the retained direction of retroversion, so that the shaft 31 is rotated on itself until this retroversion rod is aligned with the patient's forearm.

A guide pin 40, at the pointed distal end 41, is then introduced into the tube 35, from the free end thereof, and is inserted into the humeral epiphysis E over a substantial depth, as indicated by arrow 42 in FIG. 2, until its point pierces and passes at least partially through the outer cortex of the humerus H. It will be understood that the ancillary instruments 30 allows the pin to be inserted in a suitable direction relative to the humerus, the tube 35 acting as a guide for introducing and feeding through the pin. In order to prevent interference between the pin and the shaft 31, when this pin passes through the central zone of the humerus, the corresponding common part 37 of the shaft 31 advantageously tapers: this part 37 of the shaft thus has a smaller cross-section than the proximal and distal end parts forming the remainder of the shaft.

Once the guide pin 40 has reached an insertion depth in, or even through, the humerus H sufficient securely to anchor it, the ancillary instruments 30 is withdrawn, without removing the pin. The humerus is then in the state illustrated by solid lines in FIG. 3.

In a variation, when carrying out the first stage of the operation, the guide pin 40 is inserted in the humerus H without being guided, i.e. without using the ancillary instrument 30.

Figure 3:
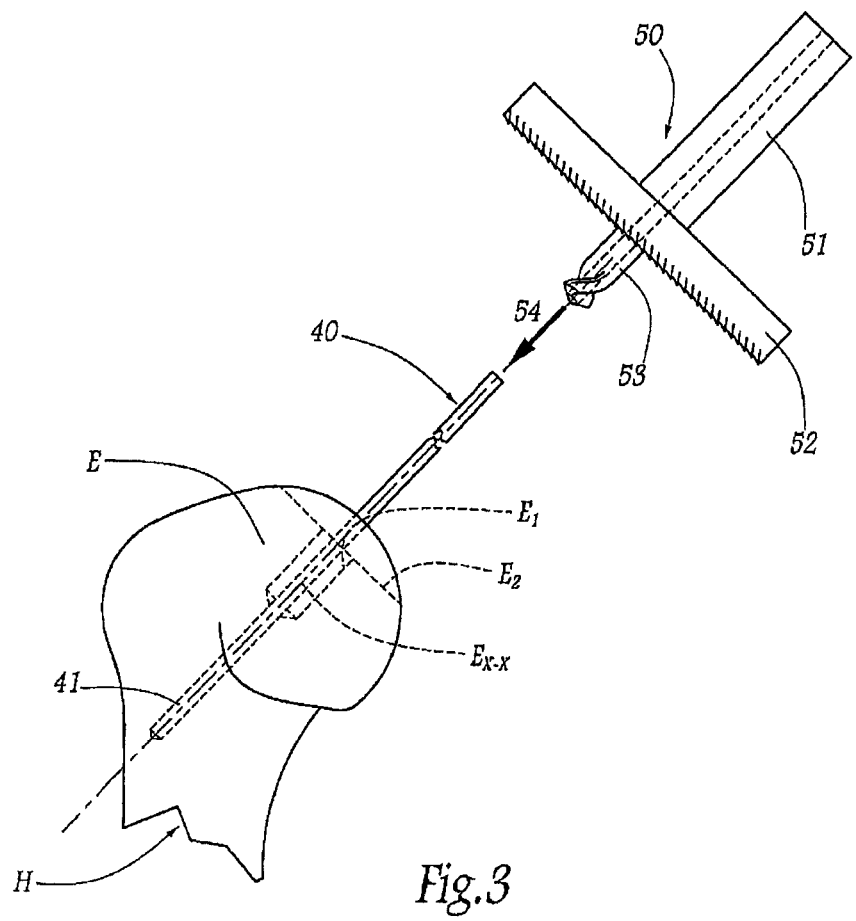
FIG. 3 is a view similar to FIG. 2, illustrating another ancillary instrument pertaining to the set of instruments, to be applied to the patient's humerus after use of the ancillary instrument of FIG. 2.

In a second stage, the surgeon will resect the end of the humeral epiphysis E, using an ancillary instrument 50 illustrated in FIG. 3. This ancillary instrument 50 comprises a tubular body 51, the internal central bore in which has a diameter equal to the external diameter of the guide pin 40. At the distal end of this body 51, the ancillary instrument 50 comprises a planar cutter 52, extending in a plane substantially perpendicular to the longitudinal axis of the body 51. In the distal projection of this cutter 52 and in a manner centered on the longitudinal axis of the body 51, the ancillary instrument 50 further comprises a terminal drill 53 internally delimiting a central bore communicating with the bore in the body 51. The external diameter of the drill 53 is provided so as to be equal to the external diameter of the anchoring tail 12 of the glenoid component 10 to be implanted, for reasons which will become apparent hereinafter.

The surgeon threads the ancillary instrument 50 around the guide pin 40, by introducing it by the terminal drill 53 thereof, as indicated by arrow 54 in FIG. 3. When this drill reaches the end of the epiphysis E, it drills the bone matter so as to form a cylindrical recess $E_1$ centered about the guide pin 40 and indicated by broken lines in FIG. 3. Similarly, as the ancillary instrument 50 moves downward along the guide pin 40, the cutter 52 gradually resects the end of the humeral epiphysis E, over a depth of a few millimeters, until there is obtained a cutting plane $E_2$ perpendicular to the guide pin 40, also indicated by broken lines in FIG. 3.

In a third stage, once the ancillary instrument 50 has been removed from the guide pin 40, the surgeon will cut the humeral epiphysis E in a manner centered on the guide pin 40, i.e. he will shape the bone matter forming this epiphysis into a cylinder $E_3$ having a center axis $E_{X-X}$ corresponding to this axis 33, as illustrated in FIG. 5. For this purpose, the surgeon uses an ancillary instrument 60 illustrated in FIG. 4. This ancillary instrument 60 comprises a central rod 61, bored internally in a manner complementary to the guide pin 40 and having an external diameter equal to that of the drill 53. This rod 61 carries, in its common part, a crown saw 62 which is of annular shape centered on the rod 61 and the distal end edge of which has teeth 63.

The rod 61 of the ancillary instrument 60 is slipped around the guide pin 40, which is left in place in the humeral epiphysis E, until its distal end is received in a complementary manner in the recess $E_1$. In doing this, the saw 62 gradually cuts out the bone matter from the epiphysis so as to obtain the bone cylinder $E_3$, it being noted that a corresponding part of the recess $E_1$ passes through the entire length of said bone cylinder. The length of the cylinder $E_3$ thus obtained, i.e. its dimension along its axis $E_{X-X}$, is determined by the depth of action of the saw 62, wherein this depth can easily be marked along the rod 61, in particular by markings.

Once the ancillary instrument 60 has been removed, the humerus H is in the state illustrated in FIG. 5.

In a fourth stage, the surgeon will remove the cylinder of bone matter $E_3$ from the humerus H using a cutting ancillary instrument 70 illustrated in FIGS. 6 and 7. This ancillary instrument comprises a tubular block 71, the internal diameter of which is equal to that of the saw 62. At its distal end, the block 71 forms a protruding outer edge 72 in which there is delimited a transverse slot 73 opening into the internal volume of the block. At its proximal end, the block 71 is closed by a base wall 74, from the central zone of which there protrudes, inside the block, a centering stud 75, the external diameter of which is equal to that of the drill 53.

After having removed the guide pin 40, the ancillary instrument 70 is slipped around the humeral cylinder $E_3$, as indicated by arrow 76 in FIG. 7. The cylinder $E_3$ is received in a complementary manner in the block 71 until the edge 72 rests against the bone surface surrounding the base of the cylinder $E_3$. A planar saw blade (not shown) is then introduced from outside into the slot 73 in order to cut the base of the cylinder $E_3$ over a cutting plane $E_4$ substantially perpendicular to the axis $E_{X-X}$ and indicated by broken lines in FIG. 7. During sawing, most of the cylinder $E_3$ is protected by the block 71 and the base wall 74, it being noted that the stud 75 is accommodated in a complementary manner in the upper end part of the central recess $E_1$.

Once the ancillary instrument 70 has been removed, the surgeon recovers the cylinder of bone matter $E_3$ thus separated from the humerus H.

In a non-illustrated variation, the slot 73 can be provided so as to be inclined relative to the longitudinal direction of the block 71 so that, in contrast to the cylinder $E_3$ described hereinbefore, the bone cylinder thus obtained has longitudinal end faces inclined relative to one another. The graft is thus able to make good the wear to a peripheral portion of the glenoid surface G, it being noted that the inclination of the slot 73 is advantageously adjustable as a function of the wear noted by the surgeon during the operation.

Before describing the following stage of the operation, namely the fifth stage, FIGS. 8 to 12, which illustrate a set of instruments forming a variation of the unit comprising the ancillary instrument 30, 50, 60 and 70 described hitherto, will now be considered.

Figure 8:
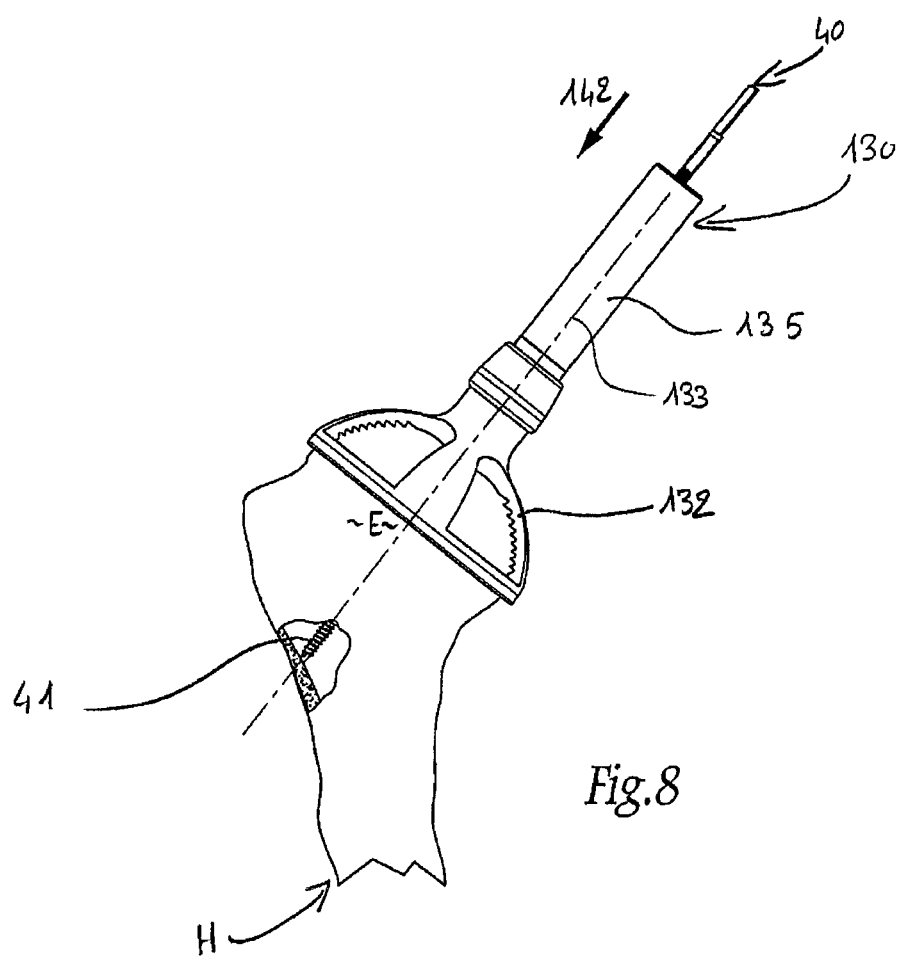

Thus, FIG. 8 shows an ancillary instrument 130 as a variation of the ancillary instrument 30 from FIG. 2. This ancillary instrument 130 comprises a distal body 132 which is functionally similar to the body 32 of the ancillary instrument 30. In particular, the body 132 is designed to cover the upper humeral epiphysis E in the manner of a cap. Unlike the body 32 of the ancillary instrument 30, the body 132 is perforated, in particular to give the surgeon a better view of the humeral epiphysis when positioning the body 132. Like the body 32 of the ancillary instrument 30, the body 132 is provided with a proximal tube 135 projecting from its external face and centered on the axis 133 round which the body 132 extends.

The ancillary instrument 130 allows the guide pin 40 to be inserted in the humeral epiphysis E so as to be close-fitted relative to the humerus H, as indicated by the arrow 142 in FIG. 8.

Figure 4:
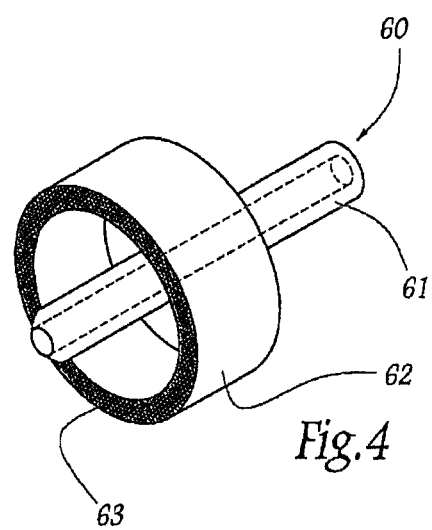
FIG. 4 is a schematic perspective view of a further ancillary instrument pertaining to the set of instruments.

As a variation of both the ancillary instrument 50 and the ancillary instrument 60 in FIGS. 3 and 4, an ancillary instrument 160 is shown in FIGS. 9 and 10. This ancillary instrument 160 comprises an elongate shaft 161 provided, at its distal end, with a crown saw 162 of annular shape centered on the shaft 161 and of which the distal end edge has teeth 163. The shaft 161 has an internal bore throughout its length so that it can be slipped, in a close-fitting and coaxial manner, round the guide pin 40 which is left in position in the humeral epiphysis E, as indicated by the arrow 164 in FIG. 9. Unlike the saw 62 of the ancillary instrument 60, the saw 162 has perforations in its lateral wall and comprises a base wall 165 which extends perpendicularly to the longitudinal direction of the shaft 161 and of which the distal face forms a planar reamer 166.

Hence, when the ancillary instrument 160 is slipped round the guide pin 40, the teeth 163 of the saw 162 gradually cut out the bone matter of the humeral epiphysis E so as to obtain the bone cylinder $E_3$. Once the entire height of the saw 162 has thus been introduced into the epiphysis, the reamer 166 begins to cut the upper end of this epiphysis and thus progressively resects this end until the cutting plane $E_2$ is obtained.

Figure 11:
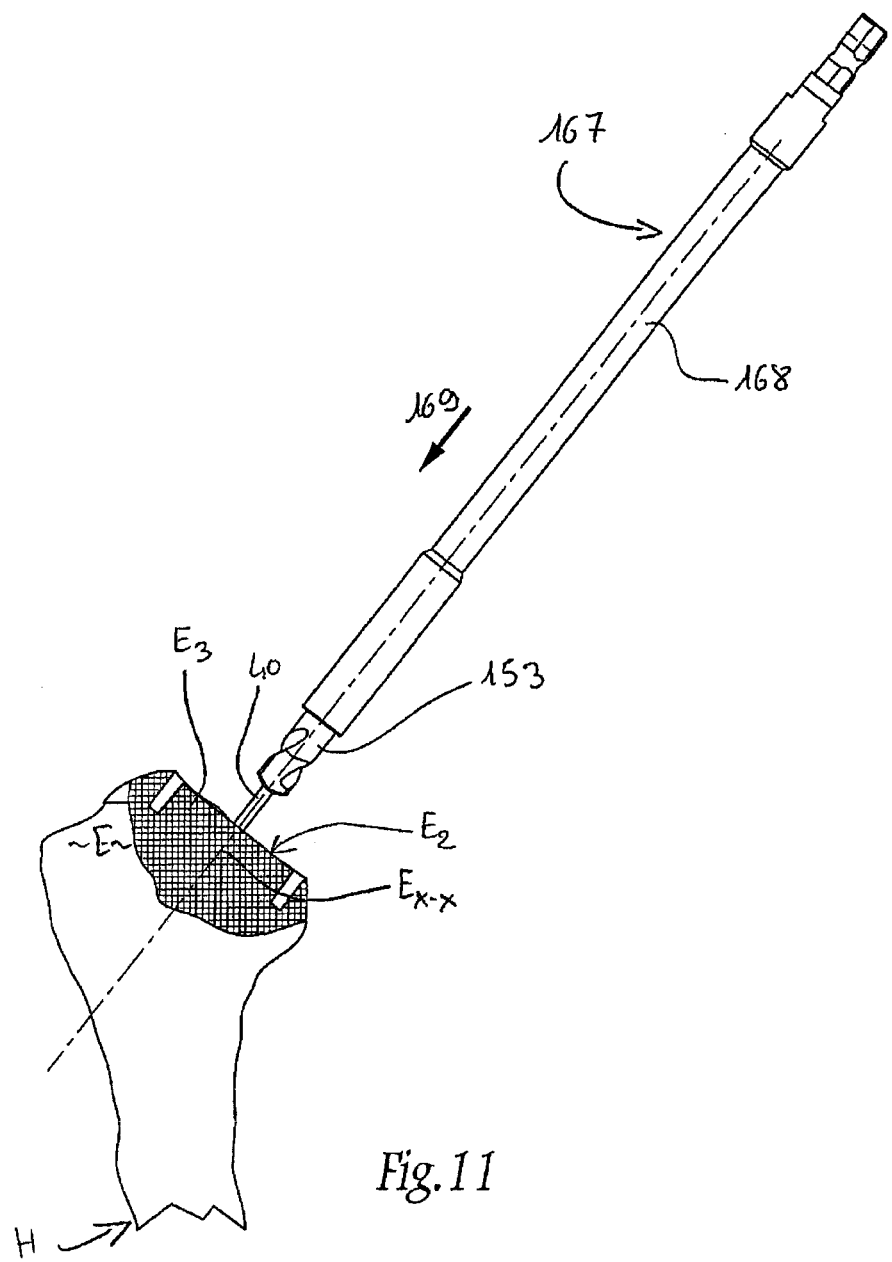

Once the ancillary instrument 160 has been released, the humerus H is in the state shown in FIG. 11.

The surgeon then uses a drilling ancillary instrument 167 comprising a bored shaft 168 of which the distal end is provided with a drill 153. By slipping the shaft 168 round the guide pin 40, as indicated by the arrow 169 in FIG. 11, the surgeon, by the action of the drill 153, digs the central part of the cylinder of bone matter $E_3$ round the guide pin 40 so as to form the recess $E_1$, centered on the axis $E_{X-X}$ of the cylinder $E_3$, as indicated in broken lines in FIG. 12, in which the ancillary instrument 168 has been released.

In practice, the drilling ancillary instrument 167 can also be used after a variation of the ancillary instrument 50, depleted of the drill 53, has been used and/or after a variation of the ancillary instrument 60, of which the rod 61 does not project on the distal side of the base wall of the saw 62 has been used.

Figure 12:
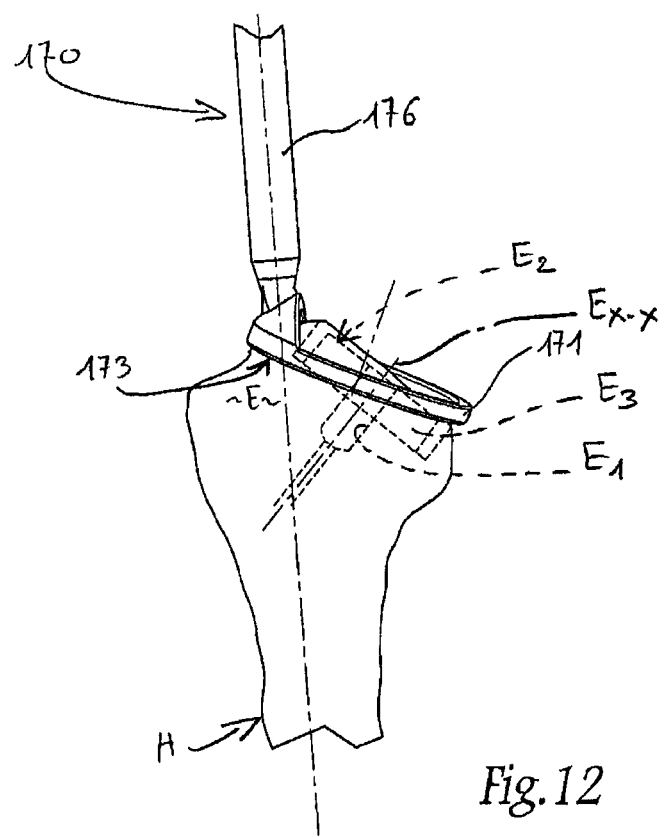

As a variation of the ancillary instrument 70 in FIGS. 6 and 7, FIG. 12 shows an ancillary instrument 170. This ancillary instrument 170 comprises an annular body 171 equipped at a point of its periphery with a proximal handling shaft 176. The annular body 171 is designed to be mounted on the humeral epiphysis E while surrounding the entire portion of the epiphysis in which the cylinder of bone matter $E_3$, previously cut out by the ancillary instrument 160, is delimited. On its distal side, the body 171 delimits a surface 173 for application and guidance of a bone cutting instrument, not shown, such as a saw blade or the like.

Hence, by manipulating the shaft 176, the surgeon positions the annular body 171 round the humeral epiphysis E so as to position the guide surface 173 in a suitable manner relative to the cylinder of bone matter $E_3$. The surgeon then applies the cutting instrument against this surface 173 in a guided manner in order to cut the base of the cylinder $E_3$ over the cutting plane $E_4$ and release this cylinder from the humerus H.

Advantageously, the guide surface 173 forms an angle of approx. 155° with the longitudinal direction of the shaft 176, and this allows the ancillary instrument 170 also to be used to prepare the implantation of the humeral component 20 at a later stage, by positioning the shaft 176 in such a way that its longitudinal direction is substantially aligned with the longitudinal direction of the humerus H, as illustrated in FIG. 12.

In a fifth stage, the cylinder of bone matter $E_3$ is used to form the bone graft 2 described hereinbefore. In order to do this, this cylinder is fitted on the glenoid surface C. The glenoid surface is previously prepared for this purpose, being opened up and, if necessary, resected. The glenoid component 10 is then implanted in the configuration described hereinbefore with reference to FIG. 1. It will be understood that the anchoring tail 12 is introduced coaxially, in a substantially close-fitting manner, into the central recess $E_1$ in the cylinder $E_3$.

If the longitudinal end faces of the bone cylinder have been formed so as to be inclined relative to each other, it will be understood that the interposing of this cylinder, as the graft, between the glenoid component 10 and the glenoid surface G allows inclination, in particular downward inclination, of the glenoid articular face 11A.

More generally, it will be understood that the dimensions desired by the surgeon for the graft 2, in particular as a function of the size of the glenoid component 10, determine the dimensions of the ancillary instrument 50, 60 and 70 or the ancillary instrument 160, 168 and 170 used to take the bone cylinder $E_3$ from the humeral epiphysis E. In particular, the internal diameter of the saw 62 or 162 determines the external diameter of the graft 2. Similarly, the depth of action of this saw determines the length 1 of the graft while at the same time allowing for any adjustment in length resulting from the positioning of the sawing slot 73 or the guide surface 173.

Furthermore, the geometry desired for the longitudinal end faces 2B and 2C of the graft 2 directly conditions the embodiment of the resection ancillary instrument 50 and cutting ancillary instrument 70 or the ancillary instrument 160 and 170, in the sense that the parts of these ancillary instrument that determine the incision profile of the bone are shaped to form an appropriate incision in the humeral epiphysis. Optionally, these ancillary instruments 50 and 70 can be associated with one or more ancillary instrument for resurfacing the longitudinal end faces of the removed cylinder $E_3$.

In practice, the surgeon also takes account of the state of the cancellous bone matter forming the epiphysis E in order, if necessary, to remove the graft with as healthy a constitution as possible. For this purpose ancillary instrument for gripping and storing the graft 2 after it has been released from the humerus H can optionally be provided, in order to limit the risks of damaging the graft.

Furthermore, in non-illustrated variations, the graft 2 can have volume forms other than a cylinder as in the FIGS., provided that the volume of bone matter forming this graft has a shape generally centered about a longitudinal axis of the type of the axis while at the same time defining a lateral face and longitudinal end faces of the type of the faces 2A, 2B and 2C. For example, the graft can thus be truncated in shape, having a longitudinal axis $E_{X-X}$; in this case, the inner surface of the crown saw 62 or 162 is, for example, provided so as to be truncated.

Figure 13:
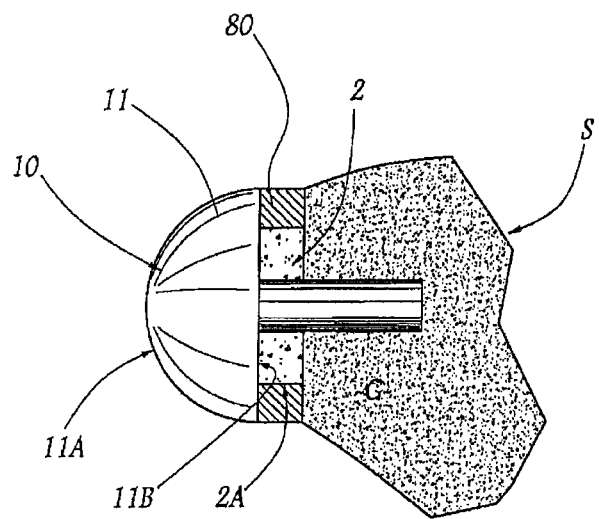
FIG. 13 is a basic schematic illustration of the glenoid part of an inverted shoulder prosthesis according to the invention.

Optionally, the bone graft 2 can be protected laterally by a reinforcing structure, such as for example ring 80 shown merely in FIG. 13. In practice, the ring 80 is configured to surround in an appropriate manner the lateral face 2A of the graft 2, over the entire length of this graft. The ring 80 is thus, in conjunction with the graft 2, interposed between the glenoid component 10 and the glenoid surface G. It will be understood that this ring can, for example, be used if the graft has, at least over a part of its length, an external diameter less than that of the glenoid head 11, the ring thus compensating for the difference in diameter.

If the ring 80 is implanted in conjunction with the graft 2, it protects the lateral face 2A of the graft and forms a support for at least a part of the face 11B of the glenoid component 10, thus limiting the stresses applied to the graft. Advantageously, the ring 80 is covered with hydroxyapatite or, more generally, has a porous or honeycomb surface state allowing improved bone adhesion and rehabilitation of the ring to the graft and to the resected surface part of the glenoid surface G that is not covered by this graft. In one embodiment, the ring 80 is attached to the glenoid component 10.

In practice, it will be understood that the inner surface of the ring 80 is advantageously complementary with the face 2A of the graft, whereas its outer face can have advantageous optional configurations. This outer surface can thus be provided so as to be truncated and diverged toward the glenoid surface G, so holes passing through the ring in respective directions substantially perpendicular to the outer surface thereof are able to receive screws or the like in order to reinforce the securing of the graft to the glenoid surface. Similarly, the bottom portion of the ring 80 can be provided so as to be less thick than the remainder of the ring so as not subsequently to disturb the humeral component 20 during adduction movements on the part of the patient.

Figure 14:
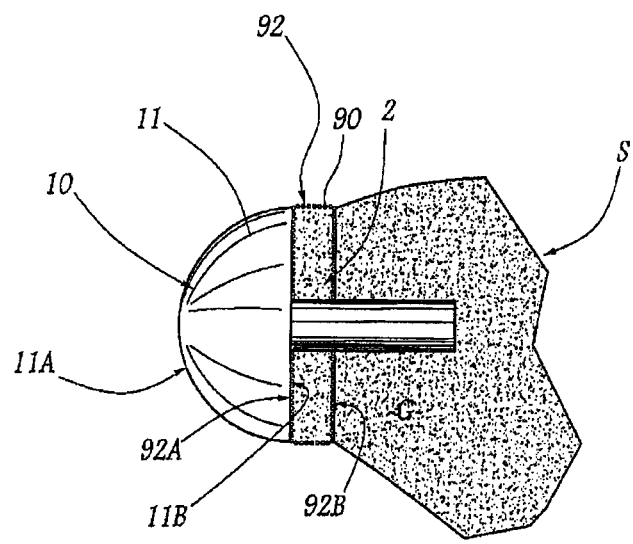
FIG. 14 is a view similar to FIG. 13 of a variation of the prosthesis according to the invention.

In a variation of the fitting method, rather than delivering a one-piece bone volume such as the cylinder $E_3$, in the upper humeral epiphysis E, the graft 2 can consist of a purée of bone substance. This substance is taken from the spongy bone zones of the humeral epiphysis, in particular when preparing the humerus for the fitting of the humeral implant. In practice, in order to contain this purée of bone substance during implantation of the glenoid component 10, a reinforcing structure, such as for example a lattice 90 shaped as a cage 92 for receiving this purée will advantageously be used, as shown in FIG. 14. The cage 92 is designed to be interposed between the glenoid component 10 and the previously prepared glenoid surface G, according to an arrangement similar to the one-piece graft illustrated in FIG. 1. In particular the cage 92 has, for example, a generally cylindrical shape of which the external diameter corresponds to that of the glenoid head 11 and of which the length corresponds to the aforementioned length 1.

The lattice 90 forming the cage 92 allows exchanges of biological fluids between the purée of bone substance with which the cage is filled and the surrounding tissues of the patient. The cage 92 thus prevents necrosis of the purée of bone substance while mechanically protecting it. In particular the cage 92 absorbs a proportion, or even the majority, of the stresses applied to the graft 2 consisting of the purée of bone substances by forming, in the region of its lateral end walls 92A and 92B, supports for the face 11B of the glenoid component 10 and the previously prepared surface of the glenoid surface G respectively. The bone substance preferably chemically bonds with the glenoid surface G through the lattice 90. In effect, the glenoid surface G is extended laterally outward to engage with the face 11B of the glenoid component 10.

In another embodiment, the cage 92 is constructed from a porous matrix or scaffold, without the purée of bone substance. The cage 92 can be, for example, reticulated bioceramic framework, structured porous tantalum, synthetic fiber mesh, and the like. The native bone of the glenoid surface G grows into the porous matrix or scaffold to create a bone graft with structure properties comparable to native bone. The cage 92 is alternately made of a slow-absorbing, biologically benign material, such as Poly-4-hydroxybutyrate (a.k.a. Tephaflex™), poly(urethane urea) (Artelon™), surgical silk, or other materials, known to the art, having similar characteristics, such as disclosed in U.S. Patent Publication No. 2007/0198087, entitled Method and Device for Rotator Cuff Repair, filed Feb. 5, 2007 and U.S. Patent Publication No. 2007/0276509, entitled Tissue Scaffold, filed Aug. 9, 2007, the entire disclosures of which are incorporated by reference. Other less preferred embodiments employ non-absorbable materials such as PTFE, Polypropylene, Nylon, or other biocompatible, inert materials known to the art.

Before or after implanting of the glenoid component 10, the humeral component 20 is implanted in the humerus H, advantageously using ancillary instrument (not shown), the handling of which is marked by the end part of the recess $E_1$ remaining in the humeral epiphysis E after removal of the bone volume such as the cylinder $E_3$. If the surgical actions applied to the humerus for implanting the component 20 by way of the recess $E_1$ are dispensed with and these actions are therefore generally independent of those applied to the humerus for taking the graft 2, the ancillary instrument 30 can be simplified, as it is in this case no longer necessary to take account of the retroversion of the patient's forearm in order to insert the guide pin 40. The shaft 31 may in this case assume the form of an intramedullary humeral rod.

According to a variation of the fitting method, the graft 2, whether in the form of a one-piece bone volume or of a purée of bone substance, is not taken from the humeral epiphysis E but rather is taken from another of the patient's bones, in particular from his ilium, or consists of an allograft or a graft of synthetic origin, it being understood that the dimensions of this synthetic graft are provided so as to be appropriate for the glenoid component 10 to be implanted, as stated hereinbefore for the removed cylinder $E_3$ or cone frustum. Obviously, the protection ring 80 and the cage 92 described hereinbefore can be used in conjunction with a graft of this type of alternative origin.

Figure 15:
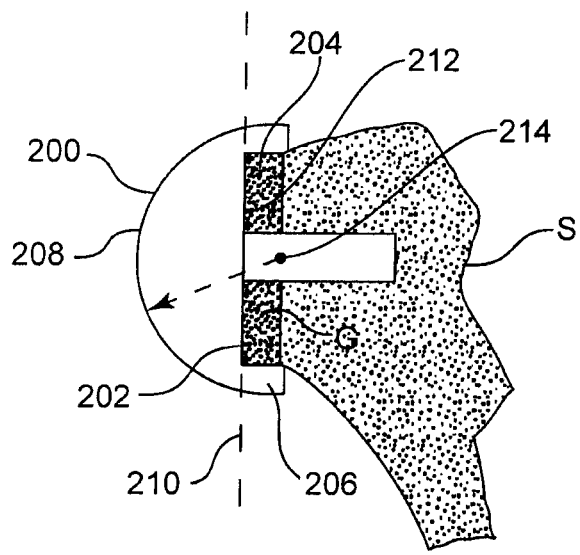
FIGS. 15-21 illustrate various uses of a bone graft to lateralize the glenoid component of an inverted shoulder prosthesis according to an embodiment of the present invention.

FIG. 15 is a schematic illustration of a glenoid component 200 of an inverted shoulder prosthesis attached to the glenoid surface G according to an embodiment of the present invention. The glenoid component 200 includes a recess 202 that substantially receives the bone graft 204. The recess 202 acts as a reinforcing structure that protects the bone graft 204 laterally, similar to the ring 80 in the embodiment of FIG. 13. Consequently, the bone graft 204 can be a one-piece bone volume or a purée of bone substance. In an embodiment where the bone graft 204 is a purée of bone substance, reinforcing fibers 279 are optionally added to the mixture. In the illustrated embodiment, lower portion 206 of the convex articular surface 208 extends beyond the pillar of the scapula S to minimize interference with the humeral prosthetic portion. The radius of curvature of convex articular surface 208 is preferably selected so the center of rotation 214 around the glenoid component 200 is preferably in plane 210 comprising a distal surface 212 of the bone graft 204 or between the plane 210 and the glenoid surface G. Once the bone graft 204 has fused with the glenoid surface G, the distal surface 212 of the bone graft 204 becomes the effective glenoid surface.

Figure 16:
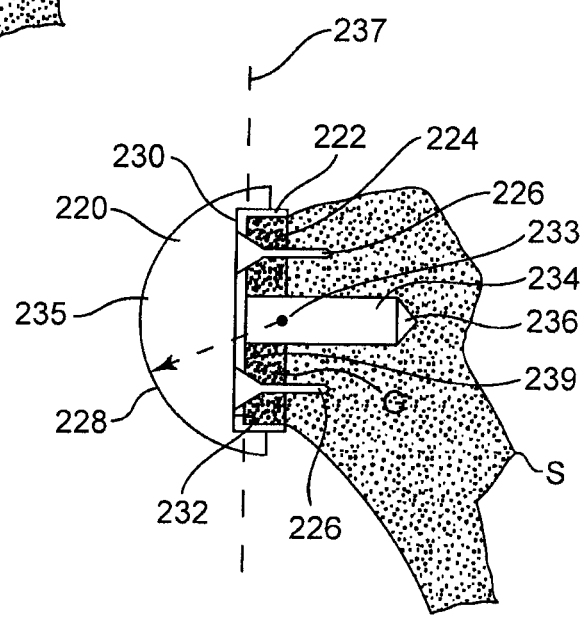

FIG. 16 is a schematic illustration of a glenoid component 220 of an inverted shoulder prosthesis attached to the glenoid surface G according to an embodiment of the present invention. Reinforcing structure 222 extends over at least a portion of the bone graft 224. The reinforcing structure 222 can be rigid or flexible. In one embodiment, the reinforcing structure 222 is constructed from a mesh material made from metal, synthetics, ceramics, or a combination thereof. Consequently, the bone graft 224 can be a one-piece bone volume or a purée of bone substance. Screws 226 optionally secure the reinforcing structure 222 and/or bone graft 224 to the glenoid surface G.

The glenoid component 220 includes a recess 230 that engages with distal surface 232 of the reinforcing structure 222. Anchor 234 optionally extends through the reinforcing structure 222 and bone graft 224 to further secure the glenoid component 220 to the scapula S. In the illustrated embodiment, the anchor 234 includes a pointed tip 236 to facilitate insertion into the glenoid surface G. The radius of curvature 228 of convex articular surface 235 is preferably selected so the center of rotation 233 of the glenoid component 220 is preferably either in or behind plane 237 comprising a distal surface 239 of the bone graft 224. Once the bone graft 224 has fused with the glenoid surface G, the distal surface 239 of the bone graft 224 becomes the effective glenoid surface.

Figure 17:
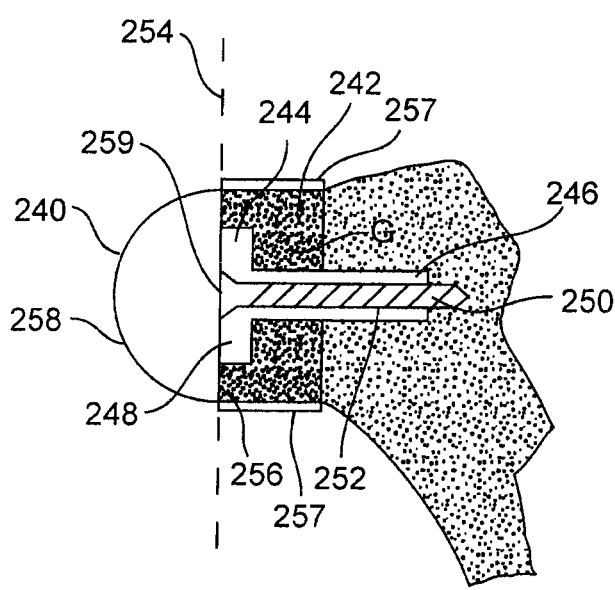

FIG. 17 is a schematic illustration of a glenoid component 240 of an inverted shoulder prosthesis attached to the glenoid surface G according to an embodiment of the present invention. Bone graft 242 is formed with a distal recess 244. Anchor 246 extends through the bone graft 242 into the glenoid surface G so that base plate 248 is positioned in the distal recess 244. Tension member 250 is optionally positioned in a center bore 252 of the anchor 246 to retain the base plate 248 against the glenoid surface G. A variety of glenoid components 240 can then be attached to the base plate 248 using a variety of attachment mechanisms. In one embodiment, the bone graft 242 is surrounded by reinforcing structure 257, such as for example a metal or synthetic mesh material. The radius of curvature of convex articular surface 258 is preferably selected so the center of rotation 259 around the glenoid component 240 is preferably in or behind a plane 254 comprising a distal surface 256 of the bone graft 242. Once the bone graft 242 has fused with the glenoid surface G, the distal surface 256 of the bone graft 242 becomes the effective glenoid surface.

Figure 18:
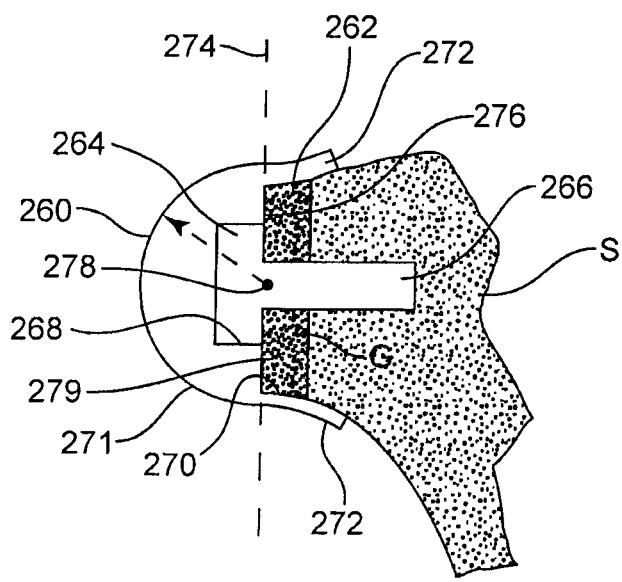

FIG. 18 is a schematic illustration of a glenoid component 260 of an inverted shoulder prosthesis attached to the glenoid surface G according to an embodiment of the present invention. Bone graft 262 is secure to the glenoid surface G using base plate 264 and anchor 266. The glenoid component 260 includes a first recess 268 sized to engage with the base plate 264 and a second recess 270 so that extensions 272 of the convex articular surface 271 extends onto a portion of the scapula S. The extensions 272 can optionally be flexible or semi-flexible to facilitate implantation. In one embodiment, the extensions 272 are attached to the scapula S using adhesives, fasteners, and the like. The bone graft 262 can be a one-piece bone volume or a purée of bone substance. The radius of curvature of convex articular surface 271 is preferably selected so the center of rotation 278 around the glenoid component 260 is preferably in or behind a plane 274 comprising a distal surface 276 of the bone graft 262.

Figure 19:
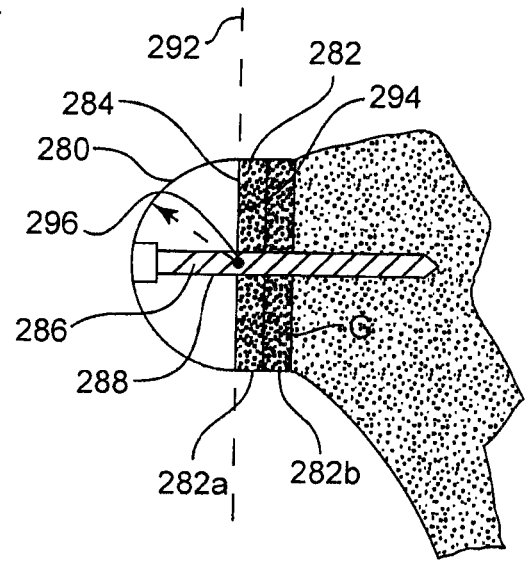

FIG. 19 is a schematic illustration of a glenoid component 280 of an inverted shoulder prosthesis attached to the glenoid surface G according to an embodiment of the present invention. Bone graft 282 is located between the glenoid surface G and the opposing surface 284 of the glenoid component 280. In the illustrated embodiment, the bone graft 282 is two or more layers 282*a*, 282*b* or bone graft material. Tension member 286 is positioned in center bore 288 to retain the glenoid component 280 against the glenoid surface G. The radius of curvature of convex articular surface 290 is preferably selected so the center of rotation 296 is in or behind plane 292 comprising distal surface 294 of the bone graft 282.

Figure 20:
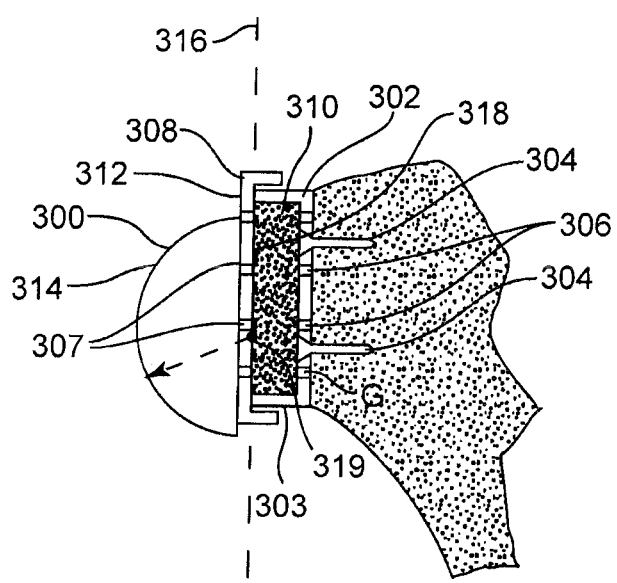

FIG. 20 is a schematic illustration of a glenoid component 300 of an inverted shoulder prosthesis attached to the glenoid surface G according to an embodiment of the present invention. Reinforcing structure 302 is attached to the glenoid surface G using fasteners 304. Side walls 303 of the reinforcing structure 302 support the outer lateral face of bone graft 310. The reinforcing structure 302 preferably has a plurality of holes or perforations 306 to facility bone in-growth.

Opposite reinforcing structure 308 extends over the reinforcing structure 302 and bone graft 310. In the illustrated embodiment, opposite reinforcing structure 308 telescopically engages with the reinforcing structure 302. The bone graft 310 can be a one-piece bone volume or a purée of bone substance. The opposite reinforcing structure 308 optionally includes a plurality of holes 307 to facilitate bone in-growth.

Glenoid component 300 is optionally attached to distal surface 312 of the opposing reinforcing structure 308. In the illustrated embodiment, the glenoid component is mounted to the opposing reinforcing structure 308 off-center. The opposing reinforcing structure 308 preferably has a plurality of mounting features that permit the surgeon to locate the glenoid component 300 in a variety of locations. The radius of curvature of convex articular surface 314 is preferably selected so the center of rotation 319 is in or behind plane 316 comprising distal surface 318 of the bone graft 310. In another embodiment, the center of rotation is close to the plane 316.

Figure 21:
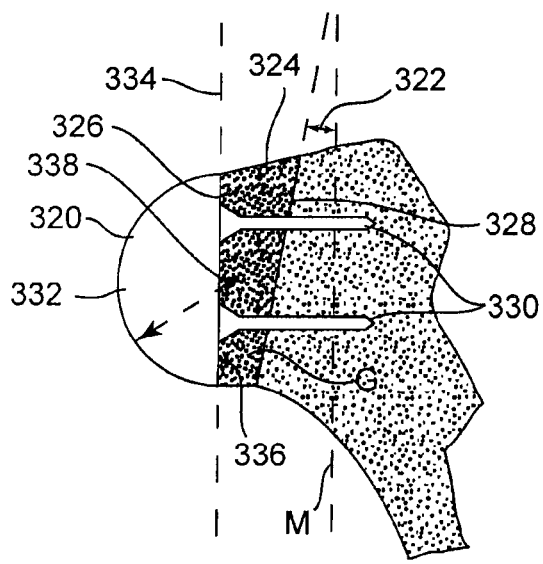

FIG. 21 is a schematic illustration of a glenoid component 320 of an inverted shoulder prosthesis attached to the glenoid surface G according to an embodiment of the present invention. The glenoid surface G is resected at an angle 322 with respect to the medial line M of the patient. In order to compensate, the bone graft 324 is formed with non-parallel faces 326, 328. In the illustrated embodiment, the bone graft 324 is secured to the glenoid surface G using fasteners 330, although any of the structures disclosed herein could be used. The radius of curvature of convex articular surface 332 is preferably selected so the center of rotation 338 is in or behind plane 334 comprising distal surface 336 of the bone graft 324.

Figure 22:
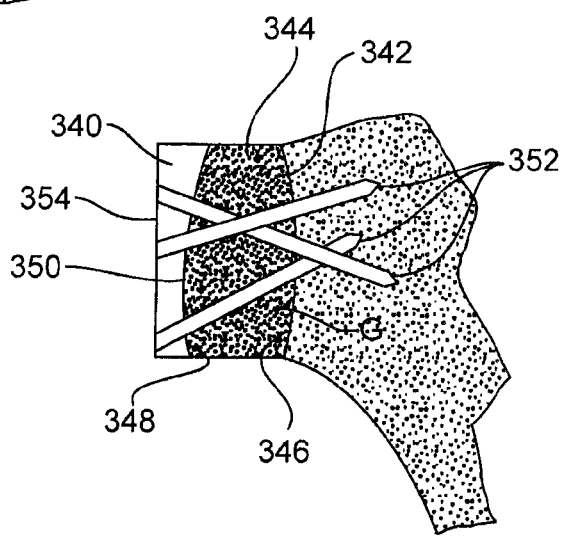
FIGS. 22-26 illustrate various uses of a bone graft to lateralize the glenoid component of an anatomical shoulder prosthesis according to an embodiment of the present invention.

FIG. 22 is a schematic illustration of a glenoid component 340 of an inverted shoulder prosthesis attached to the glenoid surface G according to an embodiment of the present invention. The exposed surface 342 of the glenoid surface G is non-planar. In order to compensate, the bone graft 344 is preferably formed with a complementary shaped surface 346. In the illustrated embodiment, opposing face 348 of the glenoid component 340 also is non-planar. Consequently, distal surface 350 of the bone graft 344 is also preferably formed with a complementary shape. The non-planar surfaces 346, 348 provide structural advantages for some applications.

In the illustrated embodiment, the glenoid component 340 is secured to glenoid surface G using a plurality of fasteners 352. Although distal surface 354 of the glenoid component 340 is illustrated as planar it can be configured for with either a convex or concave articular surface, depending on the application.

Figure 23:
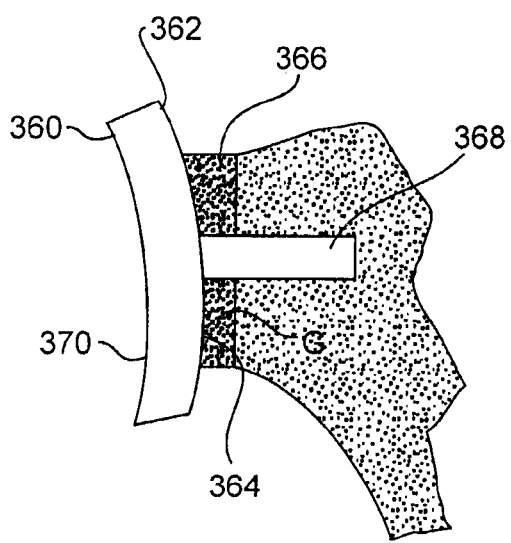

FIG. 23 is a schematic illustration of a glenoid component 360 of an anatomical shoulder prosthesis attached to the glenoid surface G according to an embodiment of the present invention. Opposing face 362 of the glenoid component 360 is non-planar. In order to compensate, distal surface 364 of the bone graft 366 is preferably formed with a complementary shape. In the illustrated embodiment, the glenoid component 360 is secured to glenoid surface G using anchor 368, although any of the securing structures disclosed herein may be used. Distal surface 370 of the glenoid component 360 is illustrated as concave, but could be convex depending on the application.

Figure 24:
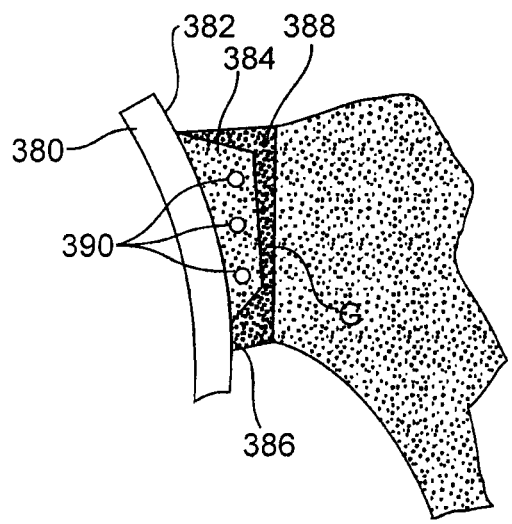

FIG. 24 is a schematic illustration of a glenoid component 380 of an anatomical shoulder prosthesis attached to the glenoid surface G according to an embodiment of the present invention. Opposing face 382 of the glenoid component 380 is non-planar and keel 384. The keel 384 optionally includes holes 390 to facilitate bone in-growth. Distal surface 386 of the bone graft 388 is preferably formed with a shape complementary to opposing surface 382. The bone graft 388 can be a one-piece bone volume or a purée of bone substance. In one embodiment, a cut-out is formed in the bone graft 388 to receive the keel 384. In another embodiment, the bone graft 388 is an annular ring and the keel is located in the center opening and secured using a purée of bone substance, bone cement, or a variety of adhesives.

Figure 25:
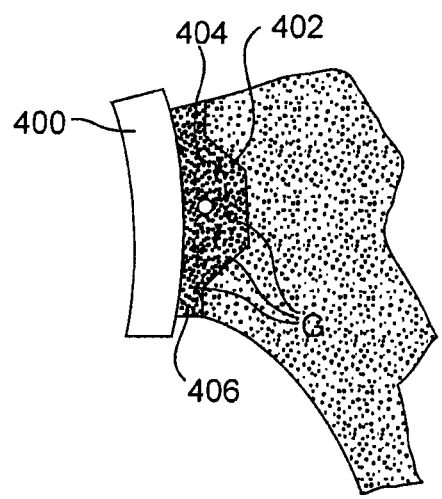

FIG. 25 is a schematic illustration of a glenoid component 400 of an anatomical shoulder prosthesis attached to the glenoid surface G according to an embodiment of the present invention. Exposed surface 402 of the glenoid surface G is non-planar. In the illustrated embodiment, the exposed surface 402 has a shape complementary to keel 404 on opposing face 406 of the glenoid component 400.

Figure 26:
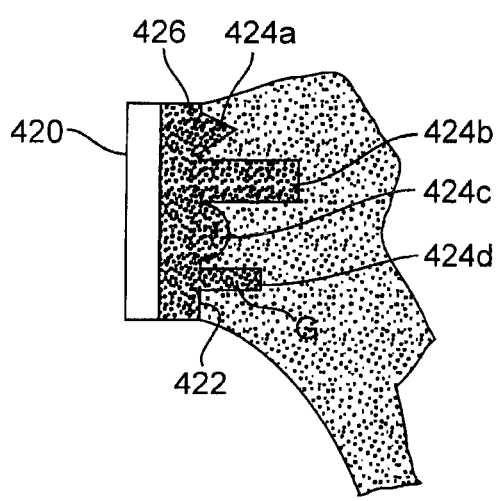

FIG. 26 is a schematic illustration of a glenoid component 420 of an inverted shoulder prosthesis attached to the glenoid surface G according to an embodiment of the present invention. Exposed surface 422 of the glenoid surface G is non-planar. In one embodiment, the various shapes 424a, 424b, 424c, 424d (collectively "424") illustrated in FIG. 26 are formed in the glenoid surface G, such as for example to remove defects in the surface of the glenoid surface G and to increase the stability of the glenoid component 420.

The bone graft 426 can be a one-piece volume, a plurality of pieces, purée of bone substance, or a combination thereof. In one embodiment, a plurality of pre-formed bone grafts of known shape are available to the surgeon during the procedure. The surgeon removes material from the exposed surface 422 of the glenoid surface G corresponding to the shape of one of the pre-formed bone grafts. The surgeon then places the pre-formed bone graft into the corresponding recess formed in the glenoid surface G.

Figure 27:
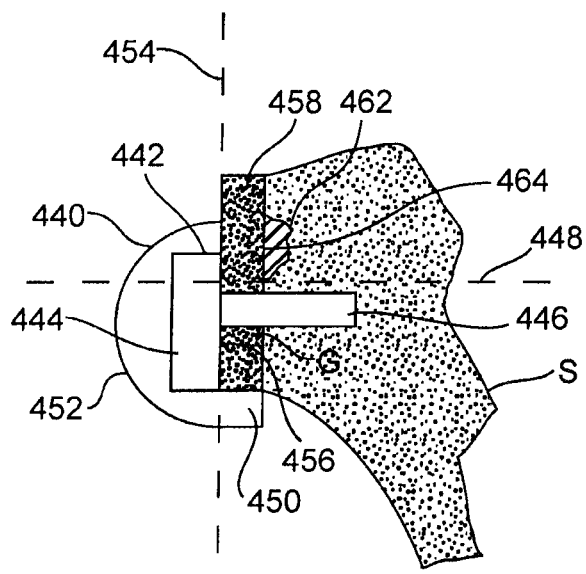
FIGS. 27-29 illustrate various uses of a bone graft to lateralize the glenoid component of an inverted shoulder prosthesis according to an embodiment of the present invention.

FIG. 27 is a schematic illustration of a glenoid component 440 of an inverted shoulder prosthesis attached to the glenoid surface G according to an embodiment of the present invention. The glenoid component 440 includes a recess 442 that engaged with base plate 444. The bone graft 458 can be a one-piece bone volume or a purée of bone substance.

In the illustrated embodiment, anchor 446 of the base plate 444 and/or the glenoid component 440 are located off-set from the center axis 448 of the glenoid surface G. Lower portion 450 of the convex articular surface 452 extends beyond the pillar of the scapula S to minimize interference with the humeral prosthetic portion. The radius of curvature of convex articular surface 452 is preferably selected so the center of rotation around the glenoid component 440 is preferably in a plane 454 comprising a distal surface 456 of the bone graft 458 or between the plane 454 and the glenoid surface G.

In the illustrate embodiment, exposed surface 460 of the glenoid surface G includes one or more defects 462. These defects 462 are preferably repaired with a one-piece bone graft, a plurality of pieces, purée of bone substance, or a combination thereof 464. After the repair, the exposed surface 460 of the glenoid surface G is preferably generally planar and well suited to receive the bone graft 458.

Figure 28:
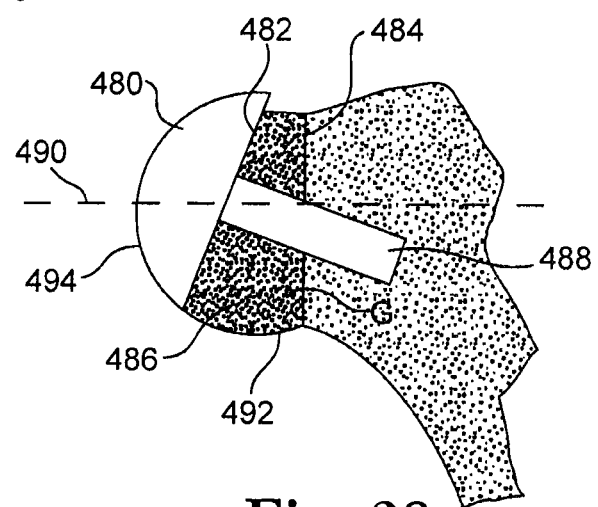

FIG. 28 is schematic illustration of a glenoid component 480 of an inverted shoulder prosthesis attached to the glenoid surface G according to an embodiment of the present invention. End faces 482, 484 of the bone graft 486 are not parallel. In the illustrated embodiment, anchor 488 of the glenoid component 480 is at an angle with respect to horizontal axis 490 of the glenoid surface G. As a result, surface 492 of the bone graft 486 acts as an extension of a lower portion of the convex articular surface 494.

Figure 29:
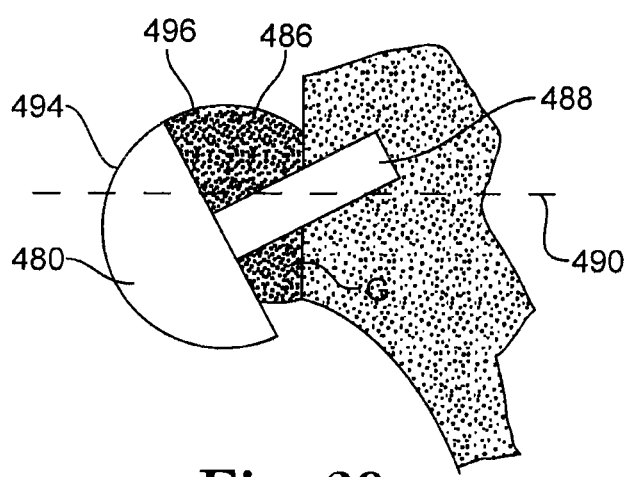

FIG. 29 is schematic illustration of the glenoid component 480 of FIG. 28 with the anchor 488 at a different angle with respect to the horizontal axis 490 of the glenoid surface G. Surface 496 of the bone graft 486 acts as an extension of an upper portion of the convex articular surface 494.

FIGS. 30A-30F illustrate an alternate method and apparatus for forming a bone graft 500 ex vivo in accordance with an embodiment of the present invention. The humeral epiphysis E is resected from the humerus H (see e.g., FIG. 7). In the illustrated embodiment, the resected humeral epiphysis E includes a planar surface P created during the resection and a curvilinear surface C.

The curvilinear surface C of the humeral epiphysis E is located on base 502, as illustrated in FIG. 30A. Cover 504 illustrated in FIG. 30B secures the humeral epiphysis E to the base 502. As illustrated in FIG. 30C, boring instrument 506 is inserted through opening 508 in the cover 504. The boring instrument 506 may be operated by hand or a motorized driver. In an alternate embodiment, the instrument 506 is an impaction instrument that does not include teeth 510.

In one embodiment, the resulting bone graft 500 is an annular ring with a planar surface 512 and a curvilinear surface 514 as illustrated in FIG. 30D. In an alternate embodiment, cutting instrument 516 is inserted through slot 518 in cover 504 so that the bone graft 500 is an annular ring with opposing planar surfaces, as illustrated in FIG. 30F.

Various modifications and additions can be made to the exemplary embodiments discussed without departing from the scope of the present invention. For example, the distal surfaces of the glenoid components disclosed herein can be used with an interpositional implant, such as disclosed in U.S. Pat. Nos. 6,436,146; 5,723,018; 4,846,840; 4,206,517; and U.S. Provisional Application Ser. No. 61/015,042, entitled INTRA-ARTICULAR JOINT REPLACEMENT, the complete disclosures of which are hereby incorporated by reference. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for providing a glenoid assembly, the method comprising:
    providing a bone graft comprising cylindrical outer shape, a medial side, a distal side, and a passage through the bone graft from the medial side to the distal side;
    providing a glenoid component comprising an articular surface on a lateral side of the glenoid component, wherein an anchoring tail extends from a medial side of the glenoid component prior to advancing the anchoring tail through the passage of the bone graft; and
    advancing the anchoring tail through the passage of the bone graft such that the anchoring tail extends entirely through the passage from the medial side of the bone graft to the distal side of the bone graft.

2. The method of claim 1, further comprising forming the bone graft from a natural material.

3. The method of claim 2, wherein the natural material comprises a bone material from a non-human source.

4. The method of claim 1, further comprising anchoring the glenoid assembly to a glenoid surface of a scapula.

5. A surgical method for implanting a shoulder prosthesis on a glenoid surface of a scapula, the method comprising:
    engaging a medial surface of a bone graft with the glenoid surface such that a distal surface of the bone graft is extended outwardly of the glenoid vault, the distal surface of the bone graft forming an outer lateral extension of the scapula that extends laterally beyond the glenoid surface;
    engaging an opposing face of a glenoid component with the distal surface of the bone graft by advancing the glenoid component axially through the distal and medial surfaces of the bone graft; and
    anchoring the glenoid component to the glenoid surface through the bone graft.

6. The surgical method of claim 5 wherein the prosthesis comprises an inverted shoulder prosthesis and an articular surface of the glenoid component comprises a convex articular surface such that a center of rotation of the glenoid component is located in the bone graft.

7. The surgical method of claim 5 further comprising preparing the bone graft by forming a cylindrical outer shape and by forming a passage through the bone graft from the medial side to the distal side.

8. The surgical method of claim 7, wherein anchoring comprises advancing a tail of the glenoid component through the passage from the distal side to the medial side and into the glenoid surface.

* * * * *

UNITED STATES PATENT AND TRADEMARK OFFICE
CERTIFICATE OF CORRECTION

PATENT NO. : 10,413,416 B2
APPLICATION NO. : 15/338188
DATED : September 17, 2019
INVENTOR(S) : Pascal Boileau et al.

It is certified that error appears in the above-identified patent and that said Letters Patent is hereby corrected as shown below:

On the Title Page

Column 1, Item (72), Inventors, Line 2, delete "Lyons" and insert --Lyon--.

Column 1, Item (60), Related U.S. Application Data, Line 4, below "(continued)",
insert --Foreign Application Priority Data Jan. 30, 2007 (FR) 0700622-- as a new item entry.

On Page 2, Column 1, Item (56), U.S. Patent Documents, Line 7, delete "Buechel" and insert --Crep--.

On Page 3, Column 1, Item (56), U.S. Patent Documents, Line 47, delete "7,033,395" and insert --7,033,396--.

On Page 4, Column 1, Item (56), Foreign Patent Documents, Line 1, delete "1950937" and insert --19509037--.

On Page 5, Column 2, Item (56), Other Publications, Line 1, delete "7," and insert --7;--.

On Page 5, Column 2, Item (56), Other Publications, Line 2, delete "Arthroplastry," and insert --Arthroplasty,--.

In the Specification

In Column 4, Line 65, delete "matter" and insert --matter;--.

In Column 13, Line 29, delete "length 1" and insert --length l--.

In Column 13, Line 55, after "axis" insert --$E_{X-X}$,--.

In Column 14, Line 45, delete "length 1." and insert --length l.--.

Signed and Sealed this
Fourteenth Day of April, 2020

Andrei Iancu
*Director of the United States Patent and Trademark Office*